US006410023B1

(12) United States Patent
Durbin et al.

(10) Patent No.: US 6,410,023 B1
(45) Date of Patent: Jun. 25, 2002

(54) RECOMBINANT PARAINFLUENZA VIRUS VACCINES ATTENUATED BY DELETION OR ABLATION OF A NON-ESSENTIAL GENE

(75) Inventors: Anna P. Durbin, Takoma Park; Peter L. Collins, Rockville; Brian R. Murphy, Bethesda, all of MD (US)

(73) Assignee: United States of America, Washington, DC (US)

( * ) Notice: Subject to any disclaimer, the term of this patent is extended or adjusted under 35 U.S.C. 154(b) by 0 days.

(21) Appl. No.: 09/350,821

(22) Filed: Jul. 9, 1999

Related U.S. Application Data

(63) Continuation-in-part of application No. 09/083,793, filed on May 22, 1998.

(60) Provisional application No. 60/047,575, filed on May 23, 1997, and provisional application No. 60/059,385, filed on Sep. 19, 1997.

(51) Int. Cl.[7] ........................ A61K 39/12; A61K 39/00; A61K 39/155; A61K 39/165; C12P 21/06

(52) U.S. Cl. ............................... 424/186.1; 424/184.1; 424/185.1; 424/199.1; 424/211.1; 424/212.1; 435/69.1; 435/440; 435/252.3; 435/320.1

(58) Field of Search .......................... 424/184.1, 185.1, 424/186.1, 211.1, 212.1; 435/69.1, 440, 252.3, 320.1

(56) References Cited

U.S. PATENT DOCUMENTS

| | | | | |
|---|---|---|---|---|
| 5,716,821 A | 2/1998 | Wertz et al. | | 435/235.1 |
| 5,789,229 A | 8/1998 | Wertz et al. | | 435/235.1 |
| 5,869,036 A | 2/1999 | Belshe et al. | | 424/93.2 |

FOREIGN PATENT DOCUMENTS

| | | | |
|---|---|---|---|
| EP | 0 440 219 A1 | 8/1991 | |
| EP | 0 702 085 A1 | 3/1996 | |
| WO | WO 93/14207 | 7/1993 | C12N/15/45 |
| WO | WO 93/21310 | 10/1993 | |
| WO | WO 97/06270 | 2/1997 | |
| WO | WO 97/11093 | 3/1997 | |
| WO | WO 97/12032 | 4/1997 | |
| WO | WO 97/20468 | 6/1997 | |
| WO | WO 98/02530 | 1/1998 | C12N/7/04 |
| WO | WO 98/13501 | 4/1998 | C12N/15/45 |
| WO | WO 98/43668 | 10/1998 | A61K/39/155 |
| WO | WO 98/53078 | 11/1998 | C12N/15/45 |
| WO | WO 99/15631 | 4/1999 | C12N/7/04 |

OTHER PUBLICATIONS

Baron et al., "Rescue of Rinderpest Virus from Cloned cDNA," *J. Virol.* 71:1265–1271, 1997 (copy enclosed).

(List continued on next page.)

*Primary Examiner*—Hankyel T. Park
*Assistant Examiner*—Stacy S. Brown
(74) *Attorney, Agent, or Firm*—Woodcock Woodcock LLP

(57) ABSTRACT

Recombinant parainfluenza virus (PIV) are provided in which expression of the C, D and/or V translational open reading frame(s) (ORFs) is reduced or ablated to yield novel PIV vaccine candidates. Expression of the C, D and/or V ORF(s) is reduced or ablated by modifying a recombinant PIV genome or antigenome, for example by introduction of a stop codon, by a mutation in an RNA editing site, by a mutation that alters the amino acid specified by an initiation codon, or by a frame shift mutation in the targeted ORF(s). Alternatively, the C, D and/or V ORF(s) is deleted in whole or in part to render the protein(s) encoded thereby partially or entirely non-functional or to disrupt protein expression altogether. C, D and/or V ORF(s) deletion and knock out mutants possess highly desirable phenotypic characteristics for vaccine development. These deletion and knock out mutations changes specify one or more desired phenotypic changes in the resulting virus or subviral particle. Vaccine candidates are generated that show a change in viral growth characteristics, attenuation, plaque size, and/or a change in cytopathogenicity, among other novel phenotypes. A variety of additional mutations and nucleotide modifications are provided within the C, D and/or V ORF(s) deletion or ablation mutant PIV of the invention to yield desired phenotypic and structural effects.

53 Claims, 2 Drawing Sheets-

OTHER PUBLICATIONS

Bellini et al., "Measles Virus P Gene Codes for Two Proteins," *J. Virol.* 53:908–19, 1985 (copy enclosed).

Belshe et al., "Cold Adaptation of Parainfluenza Virus Type 3: Induction of Three Phenotypic Markers," *J. Med. Virol.* 10:235–42, 1982.

Blumberg et al., "Measles Virus L Protein Evidences Elements of Ancestral RNA Polymerse," *Virology* 164:487–497, 1988.

Buchholz et al., "Generation of Bovine Respiratory Syncytial Virus (BRSV) from cDNA: BRSV NS2 Is Not Essential for Virus Replication in Tissue Culture, and the Human RSV Leader Region Acts as a Functional BRSV Genome Promoter," *J. Virol.* 73:251–259, 1999 (copy enclosed).

Bukreyev, et al., "Recovery of Infectious Respiratory Syncytial Virus Expressing and Additional, Foreign Gene," *J. Virol.* 70:6634–41, 1996 (copy enclosed).

Bukreyev, et al., "Interferon γ Expressed by a Recombinant Syncytial Virus Attenuates Virus Replication in Mice Without Compromising Immunogenicity," *Proc. Natl. Acad. Sci. USA* 96:2367–2372, 1999 (copy enclosed).

Cadd et al., "The Sendai Paramyxiovirus Accessory C Proteins Inhibit Viral Genome Amplification in Promoter–Specific Fashion," *J. Virol.* 70:5067–74, 1996 (copy enclosed).

Cattaneo et al., "Measles Virus Editing Provides an Additional Cystein–Rich Protein," *Cell* 56:759–764, 1989 (copy enclosed).

Collins et al., "Rescue of Synthetic Analogs of Respiratory Syncytial Virus Genomic RNA and Effect of Truncations and Mutations on the Expression of a Foreign Reporter Gene," *Proc. Natl. Acad. Sci. USA*, 88:9663–9667, 1991 (copy enclosed).

Collins, et al., "Rescue of a 7502–Nucleotide (49.3% of Full–Length) Synthetic Analog of Respiratory Syncytial Virus Genomic RNA," *Virology* 195:252–256, 1993 (copy enclosed).

Collins, et al., "Production of Infectious Human Respiratory Syncytial Virus from Cloned cDNA Confirms an Essential Role of the Transcription Elongation Factor from the 5' Proximal Open Reading Frame of the M2 mRNA in Gene Expression and Provides a Capability for Vaccine Development," *Proc Nat. Acad. Sci. USA* 92:11563–11567, 1995.

Collins et al., "Parainfluenza Viruses", in *Fields Virology*, B. N. Fields (Knipe et al., eds.), 3rd ed., vol. 1, p. 1205–1243, Lippincott–Raven Publishers, Philadelphia, 1996.

Connors et al., "A Cold–Passaged, Attenuated Strain of Human Respiratory Syncytial Virus Contains Mutations in the F and L Genes," *Virology* 208:478–484, 1995 (copy enclosed).

Conzelmann et al., "Rescue of Synthetic Genomic RNA Analogs of Rabies Virus by Plasmid–Encoded Proteins," *J. Virol.* 68:713–719, 1994 (copy enclosed).

Conzelmann, "Genetic Manipulation of Non–Segmented Negative–strand RNA Viruses," *J. Gen. Virol.* 77:381–389, 1996.

Crowe, et al., "A Further Attenuated Derivative of a Cold–Passaged Temperature–Sensitive Mutant of Human Respiratory Synctial Virus Retains Immunogenicity and Protective Efficacy Against Wild–Type Challenge in Seronegative Chimpanzees," *Vaccine* 12:783–790, 1994 (copy enclosed).

Crowe, et al., "Acquisition of the ts Phenotype by a Chemically Mutagenized Cold–Passaged Human Respiratory Syncytial Virus Vaccine Candidate Results from the Acquisition of a Single Mutation in the Polymerase (L) Gene," *Virus Genes* 13:269–273, 1996 (copy enclosed).

Curran, et al., "Sendai Virus P Gene Produces Multiple Proteins from Overlapping Open Reading Frames," *Enzyme* 44:244–249, 1990 (copy enclosed).

Curran, et al., "The Sendai Virus Nonstructural C Proteins Specifically Inhibit Viral mRNA Synthesis," *VIrology* 189:647–656, 1992 (copy enclosed).

Delenda, et al., "Normal Cellular Replication of Sendai Virus Without the trans–Frame, Nonstructural V Protein," *Virology* 228:55–62, 1997 (copy enclosed).

Delenda et al., "Sendai Viruses with Altered P,V, and W Protein Expression," *Virology* 242:327–337, 1998 (copy enclosed).

Dimock, et al., "Rescue of Synthetic Analogs of Genomic RNA and Replicative–Intermediate RNA of Human Parainfluenza Virus Type 3," *J. Virol.* 67:2772–2778, 1993.

Durbin et al., "Minimum Protein Requirements for Transcription and RNA Replication of a Minigenome of Human Parainfluenza Virus Type 3 and Evaluation of the Rule of Six," *Virology* 234:74–83, 1997.

Durbin et al., "Recovery of Infectious Human Parainfluenza Virus Type 3 from cDNA," *Virology* 235:323–332, 1997.

Escoffier et al., "Nonstructural C Protein is Required for Efficient Measles Virus Replication in Human Peripheral Blood Cells," *J. Virol.* 73:1695–8, 1999 (copy enclosed).

Firestone et al., "Nucleotide Sequence Analysis of the Respiratory Syncytial Virus Subgroup A Cold–Passaged (cp) Temperature Sensitive (ts) cpts–248/404 Live Attenuated Virus Vaccine Candidate," *Virology* 225:419–422, 1996 (copy enclosed).

Galinski et al., "Molecular Cloning and Sequence Analysis of the Human Parainfluenza 3 Virus mRNA Encoding the P and C Proteins," *Virology* 155:46–60, 1986.

Galinski et al., "Molecular Cloning and Sequence Analysis of the Human Parainfluenza 3 Virus Gene Encoding the L Protein," *Virology* 165:499–510, 1988 (copy enclosed).

Galinski et al., "RNA Editing in the Phosphoprotein Gene of the Human Parainfluenza Virus Type 3," *Virology* 186:543–550, 1992.

Garcin et al., "A Highly Recombinogenic System for the Recovery of Infectious Sendai Paramyxovirus from cDNA: Generation of a Novel Copy–back Nondefective Interfering Virus," *EMBO J.* 14:6087–6094, 1995.

Garcin et al., "A Point Mutation in the Sendai Virus Accessory C Proteins Attenuates Virulence for Mice, But Not Virus Growth in Cell Culture," *Virology* 238:424–431, 1997 (copy enclosed).

Grosfeld et al., "RNA Replication by Respiratory Syncytial Virus (RSV) Is Directed by the N, P, and L Proteins; Transcription Also Occurs under These Conditions but Requires RSV Superinfection for Efficient Synthesis of Full–Length mRNA," *J. Virol.* 69: 5677–5686, 1995.

Hall et al., "Cold–passaged Human Parainfluenza Type 3 Viruses Contain ts and Non–ts Mutations Leading to Attenuation in Rhesus Monkeys," *Virus Res.* 22:173–184, 1992.

He et al., "Recovery of Infectious SV5 from Cloned DNA and Expression of a Foreign Gene," *Virology* 237:249–260, 1997 (copy enclosed).

Hoffman et al., "An Infectious Clone of Human Parainfluenza Virus Type 3," *J. Virol.* 71:4272–4277, 1997 (copy enclosed).

Itoh et al., "Isolation of an Avirulent Mutant of Sendai Virus with Two Amino Acid Mutations from a Highly Virulent Field Strain Through Adaption to LLC–$MK_2$ Cells," *J. Gen. Virol.* 78:3207–3215, 1997 (copy enclosed).

Jin et al., "Recombinant Human Respiratory Syncytial Virus (RSV) from cDNA and Construction of Subgroup A and B Chimeric RSV," *Virology* 251:206–214, 1998 (copy enclosed).

Juhasz et al., "The Temperature–Sensitive (ts) Phenotype of a Cold–Passaged (cp) Live Attenuated Respiratory Syncytial Virus Vaccine Candidate, Designated cpts530, Results from a Single Amino Acid Substitution in the L Protein," *J. Virol.* 71:5814–5819, 1997 (copy enclosed).

Karron et al., "A Live Attenuated Bovine Parainfluenza Virus Type 3 Vaccine is Safe, Infectious, Immunogenic, and Phenotypically Stable in Infants and Children," *J. Inf. Dis.* 171:1107–1114, 1995a.

Karron et al., "A Live Human Parainfluenza Type 3 Virus Vaccine Is Attenuated and Immunogenic in Healthy Infants and Children," *J. Inf. Dis.* 172:1445–1450, 1995b (copy enclosed).

Kato et al, "Initiation of Sendai Virus Multiplication from Transfected cDNA or RNA with Negative or Positive Sense," *Genes to Cells* 1:569–579, 1996 (copy enclosed).

Kato et al., "The Paramyxovirus, Sendai Virus, V Protein Encodeds a Luxury Function Required for Viral Pathogenesis," *EMBO. J.* 16:578–587, 1997 (copy enclosed).

Kato et al., "Importance of the Cysteine–Rich Carboxyl–Terminal Half of V Protein for Sendai Virus Pathogenesis," *J Virol. 71*:7266–7272, 1997 (copy enclosed).

Kretzchmar et al., "Normal Replication of Vesicular Stomatitis Virus Without C Proteins," *Virology* 216:309–316, 1996 (copy enclosed).

Kuo et al., "Effect of Mutations in the Gene–Start and Gene–End Sequence Motifs on Transcription of Monocistronic and Dicistronic Minigenomes of Respiratory Syncytial Virus," *J. Virol.* 70:6892–6901, 1996 (copy enclosed).

Kurotani et al., "Sendai Virus C Proteins are Categorically Nonessential Gene Products but Silencing Their Expression Severely Impairs Viral Replication and Pathogenesis," *Genes to Cells*. 3:111–124, 1998 (copy enclosed).

Lamb et al., in *The Paramyxoviruses*, D. Kingsbury (ed.), p. 181–214, Plenum Press, New York, 1991 (copy enclosed).

Latorre et al., "The Various Sendai Virus C Proteins Are Not Functionally Equivalent and Exert both Positive and Negative Effects on Viral FNA Accumulation During the Course of Infection," *J. Virol.* 72:5984–5993, 1998 (copy enclosed).

Lawson et al., "Recombinant Vesicular Stomatitis Viruses from DNA," *Proc. Natl. Acad. Sci. USA* 92:4477–4481, 1995.

Liston et al., "Ribosomal Frameshifting During Translation of Measles Virus P Protein mRNA is Capable of Directing Synthesis of a Unique Protein," *J. Virol.* 69:6742–5750, 1995 (copy enclosed).

Matsuoka et al., "The P Gene of Human Parainfluenza Virus Type 1 Encodes P and C Proteins but not a Cysteine–Rich V Protein," *J. Virol.* 65:3406–3410, 1991 (copy enclosed).

McIntosh et al., "Respiratory Syncytial Virus," in *Virology*, pp. 1046 and 1047, Fields et al., eds., 2nd ed., Raven Press, Ltd, New York, 1990 (copy enclosed).

Mink, et al., "Nucleotide Sequences of the 3' Leader and 5' Trailer Regions of Human Respiratory Syncytial Virus Genomic RNA," *Virology* 185:615–624, 1991 (copy enclosed).

Murphy et al., "Current Approaches to the Development of Vaccines Effective Against Parainfluenza and Respiratory Syncytial Viruses," *Virus Res* 11:1–15, 1988.

Palese et al., "Negative–Strand RNA Viruses: Genetic Engineering and Applications," *Proc. Natl. Acad. Sci. USA* 93:11354–11358, 1996.

Park et al., "In Vivo Model for Pseudo–Templated Transcription in Sendai Virus," *J. Virol.* 66:7033–7039, 1992 (copy enclosed).

Pastey et al., "Structure and Sequence Comparison of Bovine Respiratory Syncytial Virus Fusion Protein," *Virus. Res.* 29:195–202, 1993 (copy enclosed).

Pastey et al., "Nucleotide Sequence Analysis of the Non––Structural NS1(1C) and NS2 (1B) Protein Genes of Bovine Respiratory Syncytial Virus," *J. of Gen. Virol.* 76:193–197, 1995 (copy enclosed).

Peeters et al., "Rescue of Newcastle Disease Virus from Cloned cDNA: Evidence that Cleavability of the Fusion Protein is a Major Determinant for Virulence," *J. Virol.* 73:5001–5009, 1999 (copy enclosed).

Pelet et al., "The P Gene of Bovine Parainfluenza Virus 3 Expresses all Three Reading Frames from a Single mRNA Editing Site," *EMBO J* 10:443–448, 1991.

Radecke et al., "Rescue of Measles Viruses from Cloned DNA," *EMBO J.* 14:5773–5784, 1995.

Radecke et al., "The Nonstructural C Protein is not Essential for Multiplication of Endmonston B Strain Measles Virus in Cultured Cells," *Virology* 217:418–21, 1996 (copy enclosed).

Ray et al., "Temperature–Sensitive Phenotype of the Human Parainfluenza Virus Type 3 Candidate Vaccine Strain (cp45) Correlates with a Defect in the L Gene," *J. Virol.* 70:580–584, 1996.

Roberts et al., "Recovery of Negative–Strand RNA Viruses from Plasmid DNAs: A Positive Approach Revitalizes a Negative Field," *Virology* 247:1–6, 1998 (copy enclosed).

Sakaguchi et al., "Expression of the HN, F, NP and M Proteins of Sendai Virus By Recombinant Vaccinia Viruses and Their Contribution to Protective Immunity Against Sendai Virus Infections in Mice," *J. Gen. Virol.* 74:479–484, 1993.

Sakai et al., "Accommodation Of Foreign Genes Into The Sendai Virus Genome: Sizes Of Inserted Genes And Viral Replication," *FEBS Letters* 456:221–226, 1999 (copy enclosed).

Sanchez et al., "Cloning and Gene Assignment of mRNAs of Human Parainfluenza Virus 3," *Virology* 147:177–186, 1985 (copy enclosed).

Schneider et al., "Recombinant Measles Viruses defective for RNA Editing and V Protein Synthesis Are Viable in Cultured Cells," *Virology* 277:314–322, 1997 (copy enclosed).

Schnell et al., "Infectious Rabies Viruses from Cloned cDNA," *EMBO J.* 13:4195–4203, 1994.

Skiadopoulos et al., "Three Amino Acid Substitutions in the L Protein of the Human Parainfluenza Virus Type 3 cp45 Live Attenuated Vaccine Candidate Contribute to Its Temperature–Sensitive and Attenuation Phenotypes," *J. Virol* 72:1762–1768, 1998.

Skiadopoulos et al., "Identification of Mutations Contributing to the Temperature–Sensitive, Cold–Adapted, and Attenuation Phenotypes of the Live–Attenuated Cold–Passage 45 (cp45) Human Parainfluenza Virus 3 Candidate Vaccine," *J. Virol.* 73:1374–1381, 1999 (copy enclosed).

Spriggs et al., "Sequence Analysis of the P and C Protein Genes of Human Parainfluenza Virus Type 3: Patterns of Amino Acid Sequence Homology Among Paramyxovirus Proteins," *J. Gen. Virol.* 67:2705–2719, 1986.

Stokes et al., "The Complete Nucleotide Sequence of the JS Strain of Human Parainfluenza Virus Type 3: Comparison with the Wash/4788/57 Prototype Strain," *Virus Res.* 25:91–103, 1992.

Stokes et al., "The Complete Nucleotide Sequence of Two Cold–Adapted, Temperature–Sensitive Attenuated Mutant Vaccine Viruses (cp12 and cp45) Derived from the JS Strain and Human Parainfluenza Virus Type 3 (PIV3)," *Virus Res.* 30:43–52, 1993.

Tao et al., "Recovery of a Fully Viable Chimeric Human Parainfluenza Virus (PIV) Type 3 in Which the Hemagglutinin–Neuraminidase and Fusion Glycoprotein Have Been Replaced by Those of PIV Type 1," *J. Virol.* 72:2955–2961, 1998.

Tao et al., "A Live Attenuated Recombinant Chimeric Parainfluenza Virus (PIV) Candidate Vaccine Containing the Hemagglutinin–Neuraminidase and Fusion Glycoproteins of PIV1 and the Remaining Proteins from PIV3 Induces Resistance to PIV1 Even in Animals Immune to PIV3" *Vaccine* 17:1101–1108, 1999 (copy enclosed).

Thomas et al., "Two mRNAs That Differ by Two Nontemplated Nucleotides Encode the Amino Coterminal Proteins P and V of the Paramyxovirus SV5," *Cell* 54:891–902, 1988 (copy enclosed).

Valsamakis et al., "Recombinant Measles Viruses with Mutations in the C, V, or F Gene have Altered Growth Phenotypes In Vivo," *J. Virol.* 72:7754–7761, 1998 (copy enclosed).

van Wyke Coelingh et al., "Antigenic and Structural Properties of the Hemagglutinin–Neuraminidase Glycoprotein of Human Parainfluenza Virus Type 3: Sequence Analysis of Variants Selected with Monoclonal Antibodies Which Inhibit Infectivity, Hemagglutination, and Neuraminidase Activities," *J. Virol.* 61:1473–1477, 1987.

Vidal et al., "Editing of the Sendai Virus P/C mRNA by G Insertion Occurs during mRNA Synthesis via a Virus–Encoded Activity," *J. Virol.* 64:239–246, 1990 (copy enclosed).

Wathen et al., "Characterization of a Novel Human Respiratory Syncytial Virus Chimeric FG Glycoprotein Expressed Using a Baculovirus Vector," *J. Gen Virol.* 70:2625–2635, 1989 (copy enclosed).

Whelan et al., "Efficient Recovery Of Infectious Vesicular Stomatitis Virus Entirely From cDNA Clones," *Proc. Natl. Acad. Sci. USA* 92:8388–8392, 1995.

Whitehead et al., "A Single Nucleotide Substitution in the Transcription Start Signal of the M2 Gene of Respiratory Syncytial Virus Vaccine Candidate cpts248/404 is the Major Determinant of the Temperature–Sensitive and Attenuation Phenotypes," *Virology* 247:232–239, 1998a (copy enclosed).

Whitehead et al., "Recombinant Respiratory Syncytial Virus (RSV) Bearing a Set of Mutations from cold–Passaged RSV is Attenuated in Chimpanzees," *J. Virol.* 72:4467–4471, 1998b (copy enclosed).

Whitehead et al., "Recombinant Respiratory Syncytial Virus Bearing a Deletion of Either the NS2 or SH Gene is Attenuated in Chimpanzees," *J. Virol.* 73:3438–3442, 1999 (copy enclosed).

Durbin et al., "Mutations in the D, D, and V Open Reading Frames of Human Parainfluenza Virus Type 3 Attenuate Replication in Rodents and Primates," *Virology* 281:319–330, 1999.

Bailly et al., "A Recombinant Human Perafinfluenza Virus Type 3 (PIV3) in Which the Nucleocapsid N Protein Has Been Replaced by That of Bovine PIV3 Is Attenuated in Primates," *J. Virol.* 74(7):3188–3195, 2000.

Bukreyev et al., "Interferon γ expressed by a recombinant respiratory syncytial virus attenuates virus replication in mice without compromosing immunogenicity," *Proc. Natl. Acad. Sci. USA* 96:2367–2372, 1999.

Tao, "A live attenuated chimeric recombinant parainfluenza virus (PIV) encoding the internal proteins of PIV type 3 and the surface glycoproteins of PIV type 1 induces complete resistance to PIV1 challenge and partial resistance of PIV3 challenge," *Vaccine* 17:1100–1108, 1999.

van Wyke Coelingh et al., "Attenuation of Bovine Parainfluenza Virus Type 3 in Nonhuman Primates and Its Ability to Confer Immunity to Human Parainfluenza Virus Type 3 Challenge," *J. Infect. Dis.* 157(4):655–661, 1988.

RECOMBINANT PARAINFLUENZA VIRUS VACCINES ATTENUATED BY DELETION OR ABLATION OF A NON-ESSENTIAL GENE

CROSS-REFERENCES TO RELATED APPLICATIONS

The present application is a continuation-in-part application of, and claims the benefit under Title 35 of U.S. patent application Ser. No. 09/083,793, filed May 22, 1998, which is a continuation-in-part application of U.S. Provisional Application No. 60/047,575, filed May 23, 1997, and U.S. Provisional Application No. 60/059,385, filed Sep. 19, 1997. Each of the foregoing priority applications is incorporated herein by reference in its entirety for all purposes.

BACKGROUND OF THE INVENTION

Introduction

Human parainfluenza virus type 3 (HPIV3) is a common cause of serious lower respiratory tract infection in infants and children less than one year of age. It is second only to respiratory syncytial virus (RSV) as a leading cause of hospitalization for viral lower respiratory tract disease in this age group (Collins et al., p. 1205–1243. In B. N. Fields (Knipe et al., eds), Fields Virology, 3rd ed, vol. 1. Lippincott-Raven Publishers, Philadelphia, 1996; Crowe et al., *Vaccine* 13:415–421, 1995; Marx et al., *J. Infect. Dis.* 176:1423–1427, 1997). Infections by this virus results in substantial morbidity in children less than 3 years of age. HPIV1 and HPIV2 are the principal etiologic agents of laryngotracheobronchitis (croup) and also can cause severe pneumonia and bronchiolitis (Collins et al., 3rd ed. *In "Fields Virology,"* B. N. Fields, D. M. Knipe, P. M. Howley, R. M. Chanock, J. L. Melinck, T. P. Monath, B. Roizman, and S. E. Straus, Eds., Vol. 1, pp. 1205–1243. Lippincott-Raven Publishers, Philadelphia, 1996). In a long term study over a 20-year period, HPIV1, HPIV2, and HPIV3 were identified as etiologic agents for 6.0, 3.2, and 11.5%, respectively, of hospitalizations for respiratory tract disease accounting in total for 18% of the hospitalizations, and, for this reason, there is a need for an effective vaccine (Murphy et al., *Virus Res* 11, 1–15, 1988). The parainfluenza viruses have also been identified in a significant proportion of cases of virally-induced middle ear effusions in children with otitis media (Heikkinen et al., *N Engl J Med* 340:260–4, 1999). Thus, there is a need to produce a vaccine against these viruses that can prevent the serious lower respiratory tract disease and the otitis media that accompanies these HPIV infections.

Despite considerable efforts to develop effective vaccine therapies against HPIV, no approved vaccine agents have yet been achieved for any HPIV strain, nor for ameliorating HPIV related illnesses. To date, only two live attenuated PIV vaccine candidates have received particular attention. One of these candidates is a bovine PIV (BPIV3) strain that is antigenically related to HPIV3 and which has been shown to protect animals against HPIV3. BPIV3 is attenuated, genetically stable and immunogenic in human infants and children (Karron et al., *J. Inf. Dis.* 171:1107–14 (1995a); Karron et al., *J. Inf. Dis.* 172:1445–1450, (1995b)). A second PIV3 vaccine candidate, JS cp45 is a cold-adapted mutant of the JS wildtype (wt) strain of HPIV3 (arron et al., (1995b), supra; Belshe et al., *J. Med. Virol.* 10:235–42 (1982)). This live, attenuated, cold-passaged (cp) PIV3 vaccine candidate exhibits temperature-sensitive (ts), cold-adaptation (ca), and attenuation (att) phenotypes which are stable after viral replication in vivo. The cp45 virus is protective against human PIV3 challenge in experimental animals and is attenuated, genetically stable, and immunogenic in seronegative human infants and children (Hall et al., *Virus Res.* 22:173–184 (1992); Karron et al., (1995b), supra).

To facilitate development of PIV vaccine candidates, recombinant DNA technology has recently made it possible to recover infectious negative-stranded RNA viruses from cDNA (for reviews, see Conzelmann, *J. Gen. Virol.* 77:381–89 (1996); Palese et al., Proc. Natl. Acad. Sci. U.S.A. 93:11354–58, (1996)). In this context, recombinant rescue has been reported for infectious respiratory syncytial virus (RSV), rabies virus (RaV), vesicular stomatitis virus (VSV), measles virus (MeV), rinderpest virus, simian virus 5 (SV5), Newcastle disease virus (NDV), and Sendai virus (SeV) from cDNA-encoded antigenomic RNA in the presence of essential viral proteins (see, e.g., Garcin et al., *EMBO J.* 14:6087–6094 (1995); Lawson et al., Proc. Natl. Acad. Sci. U.S.A. 92:4477–81 (1995); Radecke et al., *EMBO J.* 14:5773–5784 (1995); Schnell et al., *EMBO J.* 13:4195–203 (1994); Whelan et al., *Proc. Natl. Acad. Sci. U.S.A.* 92:8388–92 (1995); Hoffman et al., *J. Virol.* 71:4272–4277 (1997); Kato et al., *Genes to Cells* 1:569–579 (1996), Roberts et al., *Virology* 247(1), 1–6 (1998); Baron et al., *J. Virol.* 71:1265–1271 (1997); International Publication No. WO 97/06270; Collins et al., *Proc. Natl. Acad. Sci. USA* 92:11563–11567 (1995); U.S. patent application Ser. No. 08/892,403, filed Jul. 15, 1997 (corresponding to published International Application No. WO 98/02530 and priority U.S. Provisional Application Nos. 60/047,634, filed May 23, 1997, 60/046,141, filed May 9, 1997, and 60/021,773, filed Jul. 15, 1996); Juhasz et al., *J. Virol.* 71(8):5814–5819 (1997); He et al. *Virology* 237:249–260 (1997); Baron et al. *J. Virol.* 71:1265–1271 (1997); Whitehead et al., *Virology* 247(2):232–9 (1998a); Whitehead et al., *J. Virol.* 72(5) :4467–4471 (1998b); Peeters et al. *J. Virol.* 73:5001–5009, 1999; Jin et al. *Virology* 251:206–214 (1998); Bucholz et al. *J. Virol.* 73:251–259 (1999); and Whitehead et al., *J. Virol.* 73:(4)3438–3442 (1999), each incorporated herein by reference in its entirety for all purposes).

In more specific regard to the instant invention, a method for producing HPIV with a wt phenotype from cDNA was recently developed for recovery of infectious, recombinant PIV3 JS strain (see, e.g., Durbin et al., *Virology* 235:323–332, 1997; U.S. patent application Ser. No. 09/083, 793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference). In addition, these disclosures allow for genetic manipulation of cDNA clones to determine the genetic basis of phenotypic changes in biological mutants, e.g., which mutations in the HPIV3 cp45 virus specify its ts, ca and att phenotypes, and which gene(s) of BPIV3 specify its attenuation phenotype. Additionally, these disclosures render it feasible to construct novel PIV vaccine candidates and to evaluate their level of attenuation, immunogenicity and phenotypic stability.

Thus, infectious wild type recombinant PIV3 (r)PIV3, as well as a number of ts derivatives, have now been recovered from cDNA, and reverse genetics systems have been used to generate infectious virus bearing defined attenuating mutations and to study the genetic basis of attenuation of existing vaccine viruses. For example, the three amino acid substitutions found in the L gene of cp45, singularly or in combination, have been found to specify the ts and attenuation phenotypes. Additional ts and attenuating mutations are present in other regions of the PIV3cp45. In addition a chimeric PIV1 vaccine candidate has been generated using the PIV3 cDNA rescue system by replacing the PIV3 HN and F open reading frames (ORFs) with those of PIV1 in a PIV3 full-length cDNA that contains the three attenuating mutations in L. The recombinant chimeric virus derived from this cDNA is designated rPIV3-1.cp45L (Skiadopoulos et al., *J Virol* 72:1762–8, 1998; Tao et al., *J Virol* 72:2955–2961, 1998; Tao et al., *Vaccine* 17:1100–1108, 1999, incorporated herein by reference). rPIV3-1.cp45L was attenuated in hamsters and induced a high level of resistance to challenge with PIV1. A recombinant chimeric virus, designated rPIV3-1.cp45, has been produced that contains 13 of the 15 cp45 mutations, i.e., excluding the mutations in HN and F, and is highly attenuated in the upper and lower respiratory tract of hamsters (Skiadopoulos et al., *Vaccine* In press, 1999).

Despite these numerous advances toward development of effective vaccine agents against different PIV groups, there remains a clear need in the art for additional tools and methods to engineer safe and effective vaccines to alleviate the serious health problems attributable to PIV, particularly illnesses among infants and children due to infection by HPIV3. Among the remaining challenges in this context is the need for additional tools to generate suitably attenuated, immunogenic and genetically stable vaccine candidates for use in diverse clinical settings. To facilitate these goals, existing methods for identifying and incorporating attenuating mutations into recombinant vaccine strains must be expanded. Surprisingly, the present invention fulfills this need and provides additional advantages as described hereinbelow.

SUMMARY OF THE INVENTION

The present invention provides novel tools and methods for introducing defined, predetermined structural and phenotypic changes into infectious PIV. In one embodiment of the invention, an isolated polynucleotide molecule is provided which comprises an operably linked transcriptional promoter, a polynucleotide sequence encoding a PIV genome or antigenome, and a transcriptional terminator. The genome or antigenome incorporates a knock out mutation that reduces or ablates expression of one or more of the C, D, and/or V gene(s), or a mutation that deletes all or a portion of one or more of the C, D, and/or V ORFs.

In preferred aspects of the invention, expression of one or more of the C, D, and/or V ORFs is reduced or ablated by modifying the PIV genome or antigenome to incorporate a mutation that changes the start codon from M to T for the C ORF or one or more stop codons. Alternatively, one or more of the C, D, and/or V ORFs is deleted in whole or in part or modified by other mutations such as point mutations to render the corresponding protein(s) partially or entirely non-functional or to disrupt protein expression altogether. Alternatively, mutations can be made in the editing site that prevent editing and ablate expression of proteins accessed by RNA editing (Kato et al., *EMBO* 16:578–587, 1997 and Schneider et al., *Virology*227:314–322, 1997).

The recombinant PIV of the invention having mutations in C, D, and/or V possess highly desirable phenotypic characteristics for vaccine development. The above identified modifications in the recombinant genome or antigenome specifies one or more desired phenotypic changes in the resulting virus or subviral particle. Vaccine candidates are thus generated that exhibit one or more characteristics identified as (i) a change in growth properties in cell culture, (ii) attenuation in the upper or lower respiratory tract of mammalian hosts, (iii) a change in viral plaque size, (iv) a change in cytopathic effect, and (v) a change in immunogenicity.

In exemplary PIV recombinants described herein, desired phenotypic changes include attenuation of viral growth in vitro and/or in mammalian hosts compared to growth of a corresponding wild-type or mutant parental PIV strain. In more detailed aspects, viral growth in cell culture may be attenuated by approximately 5–10-fold attributable to the knock out or gene (or genome segment) deletion mutations. Viral attenuation in the upper and/or lower respiratory tract of mammalian hosts is preferably attenuated approximately 10–100 fold, and sometimes 100–1,000 fold or greater to facilitate vaccine development. At the same time, recombinant PIV of the invention have immunogenic characteristics that stimulate a protective immune response against wt PIV challenge in both the upper and lower respiratory tracts of mammalian hosts.

The PIV genome or antigenome bearing a C, D, and/or V knockout mutation(s) can be a human or nonhuman PIV sequence, or a recombinantly modified version thereof. In one embodiment, the polynucleotide sequence encodes a chimeric genome or antigenome comprising a human PIV sequence recombinantly joined with a nonhuman PIV sequence, such as a gene or gene segment from bovine PIV (BPIV) (see, e.g., U.S. Provisional Application No. 60/143,134, filed by Bailey et al. on Jul. 9, 1999, incorporated herein by reference). In additional examples, the polynucleotide encodes a chimera of sequences from a nonhuman PIV and at least one other PIV of human or nonhuman origin.

In other embodiments, the invention provides an isolated infectious PIV particle comprising a recombinant PIV (rPIV) genome or antigenome incorporating a C, D, and/or V knockout mutation(s). The isolated infectious PIV particle can be a viral or subviral particle. As used herein, subviral particle refers to any infectious PIV particle which lacks a structural element, eg., a gene segment, gene, protein, or protein functional domain, which is present in a complete virus (eg., an assembled virion including a complete genome or antigenome, nucleocapsid and envelope). Thus, one example of a subviral particle of the invention is an infectious nucleocapsid containing a genome or antigenome, and the products of N, P, and L genes. Other subviral particles are produced by partial or complete deletions or substitutions of non-essential genes, genome segments, and/or partial or complete gene products (eg., F, HN, M, or C), among other non-essential genomic and structural elements.

In combination with the phenotypic effects provided in recombinant PIV bearing a C, D, and/or V deletion or knock out mutation(s), it is often desirable to adjust the attenuation and immunogenic phenotype by introducing additional mutations that increase or decrease attenuation and/or modulate immunogenic activity of the recombinant virus. Thus, candidate vaccine strains can be further attenuated by incorporation of at least one, and preferably two or more different attenuating mutations, for example mutations identified in a biologically derived PIV mutant or identified emprically using recombinant mini-replicons, recombinant virus, or biologically-derived virus. Preferred mutant PIV strains in this context are cold passaged (cp), cold adapted (ca), host range restricted (hr), small plaque (sp), and/or temperature sensitive (ts) mutants, for example the JS HPIV3 cp 45 mutant strain. In exemplary embodiments, one or more attenuating mutations occur in the polymerase L protein, e.g., at a position corresponding to Tyr942, Leu992, or Thr1558 of JS cp45. Alternatively, attenuating mutations in the N protein may be selected and incorporated in a C, D, and/or V deletion or knock out mutant, for example which encode amino acid substitution(s) at a position corresponding to residues Val96 or Ser389 of JS cp45. Alternative or additional mutations may encode amino acid substitution(s) in the C protein, e.g., at a position corresponding to Ile96 of JS cp45. Yet additional mutations for adjusting attenuation of a C, D, and/or V deletion or knock out mutant of the invention are found in the F protein, e.g., at a position corresponding to Ile420 or Ala450 of JS cp45, and in the HN protein, e.g., at a position corresponding to residue Val384 of JS cp45 (Skiadopoulos et al., *J. Virol.* 73:1374–1381, 1999; Skiadopoulos et al., *J Virol.* 73:1374–1381, 1999, each incorporated herein by reference).

Attenuating mutations from biologically derived PIV mutants for incorporation into C, D, and/or V deletion or knock out mutants of the invention also include mutations in noncoding portions of the PIV genome or antigenome, for example in a 3' leader sequence. Exemplary mutations in this context may be engineered at a position in the 3' leader of a recombinant virus at a position corresponding to nucleotide 23, 24, 28, or 45 of JS cp45 (Skiadopoulos et al., *J. Virol.* 73:1374–1381, 1999, incorporated herein by reference). Yet additional exemplary mutations may be engineered in the N gene start sequence, for example by changing one or more nucleotides in the N gene start sequence, e.g., at a position corresponding to nucleotide 62 of JS cp45.

From JS cp45 and other biologically derived PIV mutants, a large "menu" of attenuating mutations is provided, each of which mutations can each be combined with any other mutation(s) for adjusting the level of attenuation in a recombinant PIV bearing C, D, and/or V deletion or knock out mutation(s). For example, mutations within recombinant PIVs of the invention include one or more, and preferably two or more, mutations of JS cp45. Desired C, D, and/or V deletion or knock out mutants of the invention selected for vaccine use often have at least two and sometimes three or more attenuating mutations to achieve a satisfactory level of attenuation for broad clinical use. Preferably, recombinant PIV bearing C, D, and/or V deletion or knock out mutation (s) incorporates one or more attenuating mutation(s) stabilized by multiple nucleotide substitutions in a codon specifying the mutation.

Additional mutations which can be adopted or transferred to C, D, and/or V deletion or knock out mutants of the invention may be identified in non-PIV nonsegmented negative stranded RNA viruses and incorporated in PIV mutants of the invention. This is readily accomplished by mapping the mutation identified in a heterologous negative stranded RNA virus to a corresponding, homologous site in a recipient PIV genome or antigenome and mutating the existing sequence in the recipient to the mutant genotype (either by an identical or conservative mutation), as described in U.S. Provisional Application No. 60/129,006, filed by Murphy et al. on Apr. 13, 1999, incorporated herein by reference.

In addition to the above described mutations, infectious C, D, and/or V deletion or knock out mutants desirably incorporate heterologous, coding or non-coding nucleotide sequences from any heterologous PIV or PIV-like virus, e.g., HPIV1, HPIV2, HPIV3, bovine PIV (BPIV) or murine PIV (MPIV) to form a chimeric genome or antigenome. For example, recombinant PIV of the invention may incorporate sequences from two or more wild-type or mutant PIV strains, e.g., HPIV1 and HPIV3. Alternatively, C, D, and/or V deletion or knock out mutants of the invention may incorporate sequences from a human and non-human PIV, e.g., HPIV and BPIV. Preferably, one or more human PIV coding or non-coding polynucleotides in a "recipient" or "background" genome or antigenome are substituted with a counterpart sequence from a heterologous PIV or non-PIV virus, alone or in combination with one or more selected attenuating point mutations, e.g., cp and/or ts mutations, to yield novel attenuated vaccine strains. The isolated infectious PIV particle is preferably a human PIV, more preferably human PIV3 (HPIV3) (see, e.g., U.S. Provisional Application No. 60/143,134, filed by Bailey et al. on Jul. 9, 1999, incorporated herein by reference).

In related aspects of the invention, isolated, infectious PIV particles are provided which incorporate nucleotide sequences from HPIV3 joined to at least one sequence from a heterologous PIV, such as HPIV1, HPIV2, BPIV or MPIV. For example, entire genes of HPIV3 may be replaced by counterpart genes from other forms of PIV, such as the HN and/or F glycoprotein genes of PIV1 or PIV2. Alternatively, a selected genome segment, for example a cytoplasmic tail, transmembrane domain or ectodomain of HN or F of HPIV1 or HPIV2, can be substituted for a corresponding gene segment in a counterpart HPIV3 gene to yield constructs encoding chimeric proteins, e.g. fusion proteins having a cytoplasmic tail and/or transmembrane domain of PIV3 fused to an ectodomain of PIV1 or PIV2. Alternatively, genes or genome segments from one PIV can be added (i.e., without substitution) within a heterologous PIV background to create novel immunogenic properties within the resultant clone.

In addition to recombinant PIV having C, D, and/or V deletion or knock out mutations, the invention provides related cDNA clones, vectors and particles, each of which incorporate one or more of the subject, phenotype-specific mutations set forth herein. These are introduced in selected combinations, e.g., into an isolated polynucleotide which is a recombinant cDNA genome or antigenome, to produce a suitably attenuated, infectious virus or subviral particle upon expression, according to the methods described herein. This process, coupled with routine phenotypic evaluation, provides C, D, and/or V deletion or knock out mutants having such desired characteristics as attenuation, temperature sensitivity, altered immunogenicity, cold-adaptation, small plaque size, host range restriction, genetic stability, etc. In particular, vaccine candidates are selected which are attenuated and yet are sufficiently immunogenic to elicit a protective immune response in the vaccinated mammalian host.

In yet additional aspects of the invention, C, D, and/or V deletion or knock out mutants, with or without additional attenuating mutations adopted, e.g., from a biologically derived mutant virus, are constructed to have additional nucleotide modification(s) to yield a desired phenotypic, structural, or functional change. Typically, the selected nucleotide modification will specify a phenotypic change, for example a change in growth characteristics, attenuation, temperature-sensitivity, cold-adaptation, plaque size, host range restriction, or immunogenicity. Structural changes in this context include introduction or ablation of restriction sites into PIV-encoding cDNAs for ease of manipulation and identification.

In preferred embodiments, nucleotide changes within the genome or antigenome of a C, D, and/or V deletion or knock out mutant include modification of an additional viral gene by partial or complete deletion of the gene or reduction or ablation (knock out) of its expression. Target genes for mutation in this context include the nucleocapsid protein N, phosphoprotein P, large polymerase subunit L, matrix protein M, hemagglutinin-neuraminidase protein HN, fusion protein F. To the extent that the recombinant virus remains viable and infectious, each of these proteins can be selectively deleted, substituted or rearranged, in whole or in part, alone or in combination with other desired modifications, to achieve novel C, D, and/or V deletion or knock out mutants. For example, one or more of these genes, may be deleted in whole or in part or its expression reduced or ablated (e.g., by introduction of a stop codon, by a mutation in an RNA editing site, by a mutation that alters the amino acid specified by an initiation codon, or by a frame shift mutation) to alter the phenotype of the resultant recombinant clone to improve growth, attenuation, immunogenicity or other desired phenotypic characteristics.

Alternative nucleotide modifications in C, D, and/or V deletion or knock out mutants of the invention include a deletion, insertion, addition or rearrangement of a cis-acting regulatory sequence for a selected gene in the recombinant genome or antigenome. In one example, a cis-acting regulatory sequence of one PIV gene is changed to correspond to a heterologous regulatory sequence, which may be a counterpart cis-acting regulatory sequence of the same gene in a different PIV, or a cis-acting regulatory sequence of a different PIV gene. For example, a gene end signal may be modified by conversion or substitution to a gene end signal of a different gene in the same PIV strain. In other embodiments, the nucleotide modification may comprise an insertion, deletion, substitution, or rearrangement of a translational start site within the recombinant genome or antigenome, e.g., to ablate an alternative translational start site for a selected form of a protein.

In addition, a variety of other genetic alterations can be produced in a PIV genome or antigenome having a deletion or knock out of C, D, and/or V, alone or together with one or more attenuating mutations adopted from a biologically derived mutant PIV. For example, genes or genome segments from non-PIV sources may be inserted in whole or in part. Alternatively, the order of genes can be changed or a PIV genome promoter can be replaced with its antigenome counterpart. Different or additional modifications in the recombinant genome or antigenome can be made to facilitate manipulations, such as the insertion of unique restriction sites in various intergenic regions or elsewhere. Nontranslated gene sequences can be removed to increase capacity for inserting foreign sequences.

In yet additional aspects, polynucleotide molecules or vectors encoding the recombinant PIV genome or antigenome can be modified to encode non-PIV sequences, e.g., a cytokine, a T-helper epitope, a restriction site marker, or a protein of a microbial pathogen (e.g., virus, bacterium or fungus) capable of eliciting a protective immune response in an intended host. In one such embodiment, C, D, and/or V deletion and knock out mutants are constructed that incorporate a gene or genome segment from a respiratory syncytial virus (RSV), for example a gene encoding an antigenic protein (e.g., an F or G protein), immunogenic domain or epitope of RSV.

In related aspects of the invention, compositions (e.g., isolated polynucleotides and vectors incorporating a PIV-encoding cDNA) and methods are provided for producing an isolated infectious recombinant PIV bearing a C, D, and/or V deletion or knock out mutation(s). Included within these aspects of the invention are novel, isolated polynucleotide molecules and vectors incorporating such molecules that comprise a PIV genome or antigenome which is modified by a partial or complete deletion of the C, D, and/or V ORF(s), or one or more nucleotide changes that reduce or ablate expression thereof. Also provided is the same or different expression vector comprising one or more isolated polynucleotide molecules encoding N, P, and L proteins. These proteins also can be expressed directly from the genome or antigenome CDNA. The vector(s) is/are preferably expressed or coexpressed in a cell or cell-free lysate, thereby producing an infectious C, D, and/or V deletion or knock out mutant PIV particle or subviral particle.

The above methods and compositions for producing C, D, and/or V deletion and knock out mutant PIV yield infectious viral or subviral particles, or derivatives thereof. An infectious virus is comparable to the authentic PIV virus particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, and L proteins is an example of a subviral particle which can initiate an infection if introduced into the cytoplasm of cells. Subviral particles provided within the invention include viral particles which lack one or more protein(s), protein segment(s), or other viral component(s).

In other embodiments the invention provides a cell or cell-free lysate containing an expression vector which comprises an isolated polynucleotide molecule comprising a C, D, and/or V deletion or knock out mutant PIV genome or antigenome as described above, and an expression vector (the same or different vector) which comprises one or more isolated polynucleotide molecules encoding the N, P, and L proteins of PIV. One or more of these proteins also can be expressed from the genome or antigenome cDNA. Upon expression the genome or antigenome and N, P and L combine to produce an infectious PIV virus or subviral particle.

In other embodiments of the invention a cell or cell-free expression system (e.g., a cell-free lysate) is provided which incorporates an expression vector comprising an isolated polynucleotide molecule encoding a PIV genome or antigenome bearing a C, D, and/or V knockout mutation(s), and an expression vector comprising one or more isolated polynucleotide molecules encoding N, P, and L proteins of a PIV. Upon expression, the genome or antigenome and N, P, and L proteins combine to produce an infectious PIV particle, such as a viral or subviral particle.

The recombinant PIVs of the invention are useful in various compositions to generate a desired immune response against PIV in a host susceptible to PIV infection. Attenuated C, D, and/or V deletion and knock out mutants of the invention are capable of eliciting a protective immune response in an infected mammalian host, yet are sufficiently attenuated so as to not cause unacceptable symptoms of severe respiratory disease in the immunized host. The attenuated virus or subviral particle may be present in a cell culture supernatant, isolated from the culture, or partially or completely purified. The virus may also be lyophilized, and can be combined with a variety of other components for storage or delivery to a host, as desired.

The invention further provides novel vaccines comprising a physiologically acceptable carrier and/or adjuvant and an isolated attenuated C, D, and/or V deletion or knock out mutant PIV particle or subviral particle. In preferred embodiments, the vaccine is comprised of a C, D, and/or V deletion or knock out mutant PIV having at least one, and preferably two or more additional mutations or other nucleotide modifications as described above to achieve a suitable balance of attenuation and immunogenicity. The vaccine can be formulated in a dose of $10^3$ to $10^7$ PFU of attenuated virus. The vaccine may comprise attenuated C, D, and/or V deletion or knock out virus that elicits an immune response against a single PIV strain or against multiple PIV strains. In this regard, C, D, and/or V deletion and knock out mutant PIV can be combined in vaccine formulations with other PIV vaccine strains, or with other viral vaccine viruses such as an RSV.

In related aspects, the invention provides a method for stimulating the immune system of an individual to elicit an immune response against PIV in a mammalian subject. The method comprises administering a formulation of an immunologically sufficient amount of an attenuated, C, D, and/or V deletion or knock out mutant PIV in a physiologically acceptable carrier and/or adjuvant. In one embodiment, the immunogenic composition is a vaccine comprised of a C, D, and/or V deletion or knock out mutant PIV having at least one, and preferably two or more attenuating mutations or other nucleotide modifications specifying a desired phenotype as described above. The vaccine can be formulated in a dose of $10^3$ to $10^7$ PFU of attenuated virus. The vaccine may comprise attenuated C, D, and/or V deletion or knock out mutant PIV virus that elicits an immune response against a single PIV, against multiple PIVs, e.g., HPIV1 and HPIV3, or against one or more PIV(s) and a non-PIV pathogen such as RSV. In this context, C, D, and/or V deletion and knock out mutant PIV can elicit a monospecific immune response or a polyspecific immune response against multiple PIVs, or against one or more PIV(s) and a non-PIV pathogen such as RSV. Alternatively, C, D, and/or V deletion and knock out mutant PIV having different immunogenic characteristics can be combined in a vaccine mixture or administered separately in a coordinated treatment protocol to elicit more effective protection against one PIV, against multiple PIVs, or against one or more PIV(s) and a non-PIV pathogen such as RSV. Preferably the immunogenic composition is administered to the upper respiratory tract, e.g., by spray, droplet or aerosol. Preferably the immunogenic composition is administered to the upper respiratory tract, e.g., by spray, droplet or aerosol.

DESCRIPTION OF THE SPECIFIC EMBODIMENTS

The present invention provides recombinant PIV (rPIV) in which expression of one or more of the C, D, and or V ORFs is reduced or ablated to yield an assemblage of novel PIV vaccine candidates. Expression of the C, D, and/or V, ORFs is reduced or ablated by modifying a recombinant PIV genome or antigenome to incorporate a mutation that changes the coding assignment of the initiation codon of the C ORF or one or more stop codons in the C, D, and/or V ORF. Other alterations to achieve disruption of C, D, and/or V expression or expression or function of corresponding protein(s) to generate attenuated PIV vaccine candidates include partial or complete deletion of the C, D, and/or V coding sequence(s), in whole or in part, to render the C, D, and/or V protein(s) partially or entirely non-functional or terminate its expression.

HPIV3 is a member of the newly named Respirovirus genus of the Paramyxoviridae family in the order Mononegavirales. Its genome is a single strand of negative-sense RNA 15462 nucleotides (nt) in length (Galinski et al., *Virology* 165: 499–510, (1988); Stokes et al., *Virus Res.* 25:91–103 (1992)). At least eight proteins are encoded by PIV3: the nucleocapsid protein N, the phosphoprotein P, the nonstructural protein C, the D protein, the matrix protein M, the fusion glycoprotein F, the hemagglutinin-neuraminidase protein HN, and the large polymerase protein L (Collins et al., p. 1205–1243. In B. N. Fields (Knipe et al., eds), Fields Virology, 3rd ed, vol. 1. Lippincott-Raven Publishers, Philadelphia, 1996).

The M, HN, and F proteins are envelope-associated, and the latter two are surface glycoproteins which, as is the case with each PIV, are the major neutralization and protective antigens (Collins et al., 3rd ed. In "*Fields Virology*" (B. N. Fields, D. M. Knipe, P. M. Howley, R. M. Chanock, J. L. Melnick, T. P. Monath, B. Roizman, and S. E. Straus, Eds.), Vol. 1, pp. 1205–1243. Lippincott-Raven Publishers, Philadelphia, 1996). The significant sequence divergence between comparable PIV HN or F proteins among the PIVs is thought to be the basis for the type specificity of the protective immunity (Collins et al., 3rd ed. In *"Fields Virology"* (B. N. Fields, D. M. Knipe, P. M. Howley, R. M. Chanock, J. L. Melnick, T. P. Monath, B. Roizman, and S. E. Straus, Eds.), Vol. 1, pp. 1205–1243. Lippincott-Raven Publishers, Philadelphia, 1996; Cook et al.,. *Amer Jour Hyg* 77:150–159, 1963; Ray et al., *J Infect Dis* 162:746–9, 1990).

Figure 1:
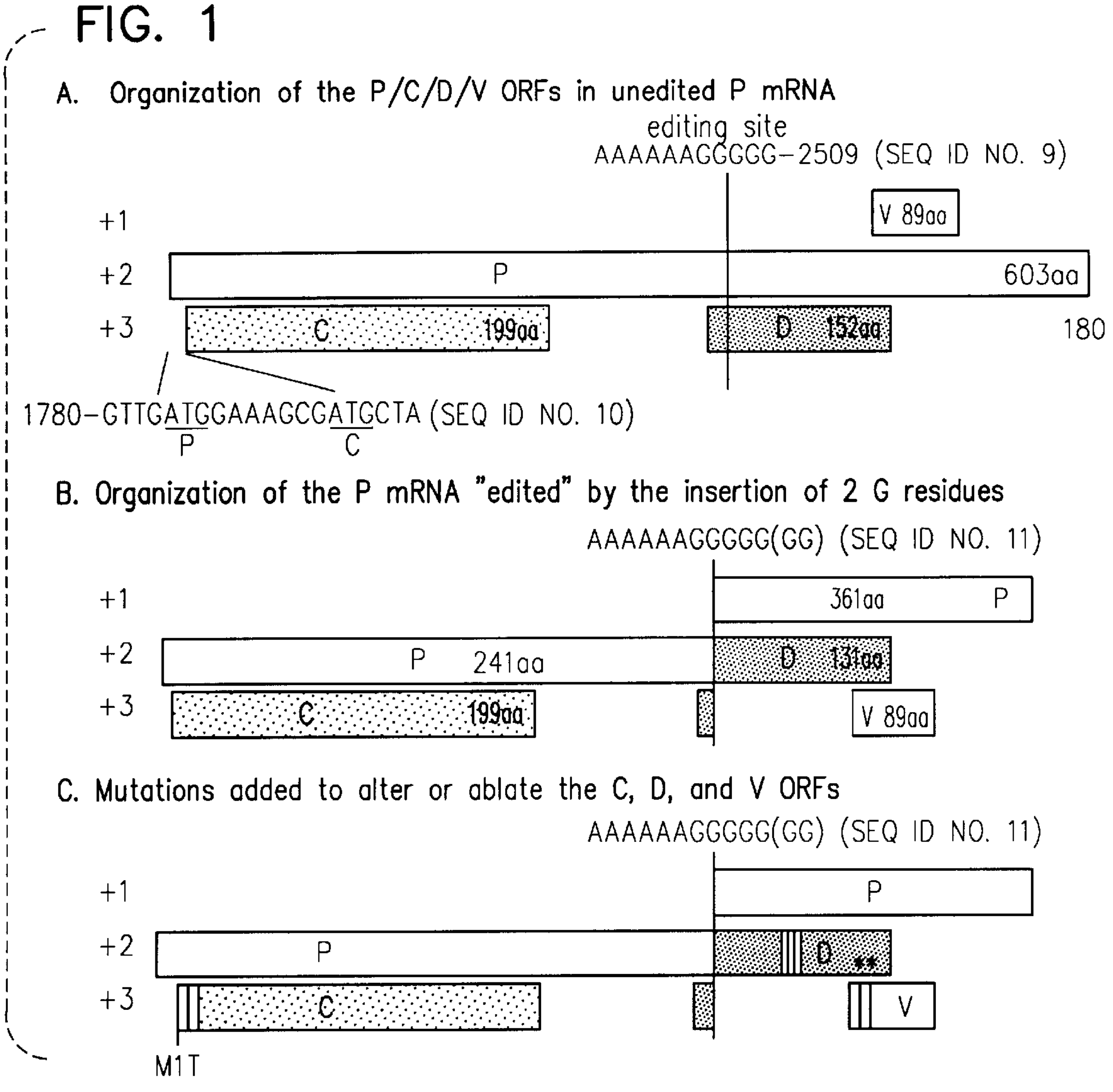
FIG. 1 depicts organization of the HPIV3 P/C/D/V ORFs (not to scale). The three reading frames of the P mRNA are shown (+1, +2 and +3) with the P, C, D and V ORFs represented by rectangles. Amino acid lengths are indicated. The position of the RNA editing site is shown as a vertical line and its sequence motif is shown and numbered according to its nucleotide position in the complete HPIV3 antigenomic sequence. Panel A details organization of the unedited P mRNA. The sequence containing the translational start sites of the P and C ORFs is shown and is numbered according to the complete antigenomic sequence. The nucleotide positions of the P, C, D, and V ORFs in the complete antigenomic sequence of the JS wild type clone are: P, 1784-3595; C, 1794-2393; D, 2442-2903; V, 2792-3066. Relative to the P mRNA, the AUG that opens the P ORF is at positions 80–82. Panel B details organization of an edited version of the P mRNA that contains an insertion of two nontemplated G residues (GG) in the editing site. This changes the reading register so that the upstream end of the P ORF in frame +2 is fused to the D ORF in frame +3. The resulting chimeric protein contains the N-terminal 241 amino acids encoded by the P ORF fused to the C-terminal 131 amino acids encoded by the D ORF. Panel C shows the positions of exemplary mutations which interrupt the C, D and V ORFs, illustrated on the edited version of the P mRNA from Panel B. Introduced stop codons are indicated by vertical lines within rectangles. The C ORF was modified to change codon 1 from M to T, and codons 7 and 26 to create stop codons. The D ORF was modified to introduce stop codons at codons 304, 305 and 306, numbered according to the 372-amino acid chimeric D protein containing the N-terminal 241 amino acids of P fused to the C-terminal 131 amino acids of D. The V ORF was modified to introduce stop codons at codons 17 and 20. These latter two mutations resulted in amino acid substitutions at codons 354 and 357 of the D ORF (asterisks).
Figure 2:
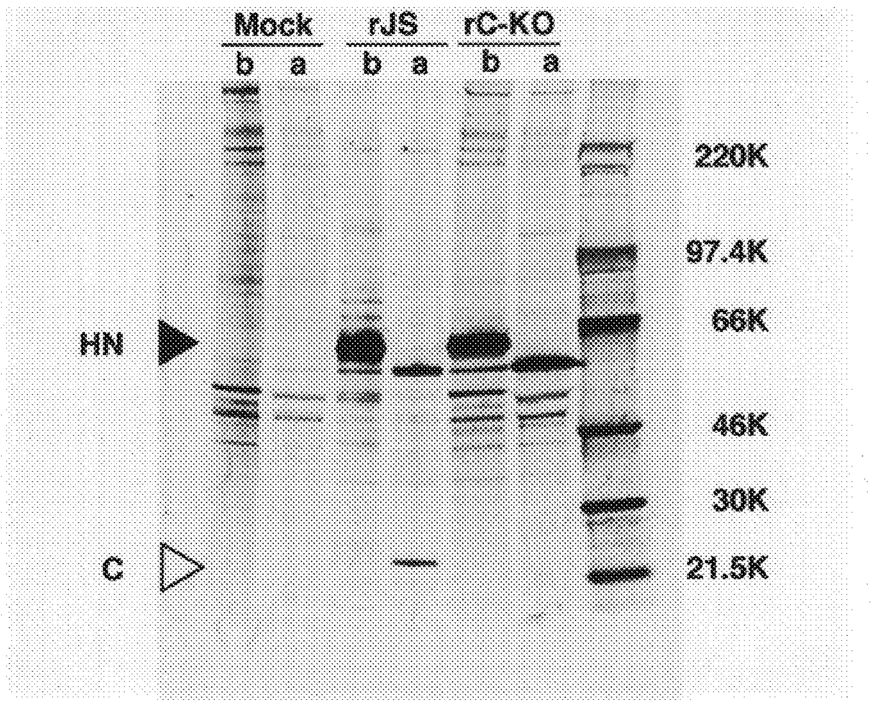
FIG. 2 provides a radioimmunoprecipitation assay demonstrating that expression of the C protein has been abrogated in the virus rC-KO. Lane (a)$^{35}$S-labeled cell lysates were immunoprecipitated with a polyclonal C-specific rabbit antiserum. A 22 kD band corresponding to the C protein (open arrow) is clearly present in rJS but absent from lane (a) of rC-KO. Lane (b): cell lysates were immunoprecipitated by a mixture of two monoclonal antibodies specific to the HPIV3 HN protein. The 64kD band corresponding to the HN protein (closed arrow) is present in both virus lysates confirming they are indeed HPIV3 and express similar levels of proteins.

The HPIV3 genes are each transcribed as a single mRNA that encodes a single protein, with the exception of the P mRNA which contains four ORFs, namely P, C, D and V (FIG. 1) (Galinski et al., *Virology* 186:543–550, 1992; Spriggs et al., *J. Gen Virol.* 67:2705–2719, 1986). The P and C proteins are translated from separate, overlapping ORFs in the mRNA (FIG. 1). Whereas all paramyxoviruses encode a P protein, only members of the genus Respirovirus and Morbillivirus encode a C protein. Individual viruses vary in the number of proteins expressed from the C ORF and in its importance in replication of the virus in vitro and in vivo. Sendai virus (SeV) expresses four independently initiated proteins from the C ORF: C', C, Y1, and Y2, whose translational start sites appear in that order in the mRNA (Curran, et al., *Enzyme* 44:244–9, 1990; Lamb et al., p. 181–214. In D. Kingsbury (ed.), The Paramyxoviruses. Plenum Press, New York, 1991), whereas HPIV3 and measles virus (MV) express only a single C protein (Bellini et al., *J Virol.* 53:908–19, 1985; Sanchez et al., *Virology* 147:177–86, 1985; Spriggs et al., *J Gen Virol.* 67:2705–2719, 1986).

A viable recombinant SeV in which all four C-derived proteins were ablated replicated inefficiently in vitro (Kurotani et al., *Genes Cells.* 3:111–124, 1998), whereas ablation of individual C proteins had complex effects (Cadd et al., *J Virol.* 70:5067–74, 1996; Curran, et al., *Virology* 189:647–56, 1992; Latorre et al., *J Virol.* 72:5984–93, 1998). A recombinant SeV bearing a single point mutation resulting in a phenylalanine (F) to serine (S) substitution at amino acid position 170 of the C protein was attenuated in mice, but its replication in cell culture was not impaired (Garcin et al., *Virology* 238:424–431, 1997; Itoh et al., *J Gen Virol.* 78:3207–15, 1997). In marked contrast to SeV, a C-minus measles virus (MV) replicated efficiently in Vero cells (Radecke et al., *Virology* 217:418–21, 1996), although it exhibited restriction of replication in human peripheral blood cells and appeared to be somewhat attenuated in vivo (Escoffier et al., *J Virol.* 73:1695–8, 1999; Valsamakis et al., *J Virol.* 72:7754–61, 1998).

In addition to the P and C ORFs, the P mRNA of PIV3 has two other ORFs, namely, D and V. The PIV3 D protein, a fusion protein of the P and D ORFs, is expressed from the P gene by the process of transcriptional editing, or RNA editing, in which two nontemplated G residues are added to the P mRNA at the RNA editing site (FIG. 1) (Galinski et al., *Virology* 186:543–550, 1992; Pelet et al., *Embo J.* 10:443–8, 1991). BPIV3 is the only other paramyxovirus which expresses a D protein and it does so by the same mechanism.

Nearly all members of the genus Respirovirus, Rubulavirus, and Morbillivirus express a V protein. The one member which clearly does not is HPIV1, which lacks an intact V ORF (Matsuoka et al., *J Virol.* 65:3406–10, 1991, incorporated herein by reference). The V ORF is characterized by the presence of a cysteine-rich domain that is highly conserved (Cattaneo et al., *Cell* 56:759–64, 1989; Park et al., *J Virol* 66:7033–9, 1992; Thomas et al., *Cell* 54:891 –902, 1988; Vidal et al., *J Virol* 64:239–46, 1990, each incorporated herein by reference). The V ORF is maintained in each of the HPIV3 viruses sequenced to date suggesting that this ORF is expressed and retains function for this virus (Galinski et al., *Virology* 155:46–60, 1986; Spriggs et al., *J Gen Virol* 67:2705–2719, 1986; Stokes et al., *Virus Res* 25:91–103, 1992).

The BPIV3 V protein is expressed when one nontemplated G residue is added at the RNA editing site (Pelet et al., *Embo J* 10:443–8, 1991, incorporated herein by reference). However, in the case of HPIV3, two to four translation stop codons lie between the editing site and the V ORF, and it is not clear whether HPIV3 represents another example in which this ORF is not expressed, or whether it is expressed by some other mechanism. One possibility is that HPIV3 editing also occurs at a second, downstream site in the P gene, although this did not appear to occur in cell culture (Galinski et al., *Virology* 186:543–550, 1992, each incorporated herein by reference). Alternatively, it might be that ribosomes gain access to the V ORF by ribosomal frameshifting. This would be comparable to the situation with the P locus of MV. MV expresses C, P, and V proteins, but also expresses a novel R protein which is synthesized by frameshifting from the P ORF to the V ORF (Liston et al., *J Virol.* 69:6742–50, 1995, incorporated herein by reference).

Although the means by which HPIV3 expresses its V protein is unclear, the extreme conservation of the its V ORF in different strains suggests that it is indeed expressed. The function of the V protein is not well defined, but V-minus MV and SeV recombinants have been recovered that replicate efficiently in vitro but exhibit reduced replication in vivo (Delenda, et al., *Virology* 228:55–62, 1997; Delenda et al., *Virology* 242:327–37, 1998; Kato et al., *Embo J.* 16:578–587, 1997; Kato et al., *J Virol.* 71:7266–7272, 1997; Valsamakis et al., *J Virol.* 72:7754–61, 1998).

The viral genome of PIV also contains extragenic leader and trailer regions, possessing promoters required for viral replication and transcription. Thus, the PIV genetic map is represented as 3' leader-N-P/C/D/V-M-F-HN-L-5' trailer. Transcription initiates at the 3' end and proceeds by a sequential stop-start mechanism that is guided by short conserved motifs found at the gene boundaries. The upstream end of each gene contains a gene-start (GS) signal, which directs initiation of its respective mRNA. The downstream terminus of each gene contains a gene-end (GE) motif which directs polyadenylation and termination. Exemplary sequences have been described for the human PIV3 strains JS (GenBank accession number Z11575, incorporated herein by reference) and Washington (Galinski M. S. In Kingsbury, D. W. (Ed.), the Parayxoviruses, pp. 537–568, Plenum Press, New York, 1991, incorporated herein by reference), and for the bovine PIV3 strain 910N (GenBank accession number D80487, incorporated herein by reference).

As used herein, "PIV gene" generally refers to a portion of the PIV genome encoding an mRNA and typically begins at the upstream end with a gene-start (GS) signal and ends at the downstream end with the gene-end (GE) signal. The term PIV gene is also interchangeable with the term "translational open reading frame", or ORF. In addition to genes, the viral genome of PIV also contains noncoding, intergenic sequences, and extragenic leader and trailer regions possessing promoters required for viral replication and transcription. Thus, the PIV genetic map is partially represented as 3' leader-N-P/C/D/V-M-F-HN-L-5' trailer. Transcription initiates at the 3' end and proceeds by a sequential stop-start mechanism that is guided by short conserved motifs found at the gene boundaries. To construct C, D, and/or V deletion mutants of the invention, one or more PIV gene(s) may be deleted in whole or in part. This means that partial or complete deletions may be made in open reading frames and/or cis-acting regulatory sequences of any one or more of the PIV genes. By "genome segment" is meant any length of continuous nucleotides from the PIV genome, which might be part of an ORF, a gene, or an extragenic region, or a combination thereof.

Alternative means for constructing C, D, and/or V mutants of the invention involve construction of "knock out" viruses to reduce or ablate gene expression without deletion of substantial portions of the PIV genome. In particular, expression of the C, D, and/or V ORF(s) is preferably reduced or ablated by modifying the recombinant PIV genome or antigenome by introduction of a stop codon, by a mutation in an RNA editing site, by a mutation that alters the amino acid specified by an initiation codon, or by a frame shift mutation in the targeted ORF(s). In one embodiment, a mutation can be made in the editing site that prevents editing and ablates expression of proteins whose mRNA is generated by RNA editing (Kato et al., *EMBO* 16:578–587, 1997 and Scnneider et al., *Virology* 227:314–322, 1997, incorporated herein by reference).

In alternative aspects of the invention, the PIV genome or antigenome is subjected to mutagenesis to generate one or more stop codons in the C, D, and/or V ORF(s). In one example, a methionine initiation codon is changed to threonine in the C ORF. In another example, two stop codons are introduced by mutations at nucleotide position (nt) 1795 (changing T to C) and nt 1813 (changing C to A) in the genome or antigenome that introduce stop codons corresponding to positions 7 and 26 of the C ORF. This generates a C knock out mutant virus designated as rC-KO. In three other mutant viruses exemplifying the invention, the D and V ORFs were interrupted singly and in combination. In the single, D knock out mutant, designated rD-KO, mutations were introduced to interrupt expression of the D ORF, which introduced C to A changes at nt positions 2692, 2695, and 2698 of the full length antigenome. These point mutations created three successive stop codons in the putative D ORF which result in premature termination of the D protein following codon 303 within a 372-amino acid chimeric D protein. In other detailed aspects, a single, V knockout mutant, rV-KO, was constructed by introducing two point mutations at nt positions 2845 (A to T) and 2854 (C to T) of the full-length antigenome. These mutations created stop codons early (aa positions 17 and 20) in the putative V ORF. The changes in rD-KO and rV-KO were collectively introduced in a single clone to create a combinatorial DV knock out mutant, rDV-KO.

As noted above, the recombinant PIV of the invention bearing one or more mutations in the C, D, and/or V ORF(s) possess highly desirable phenotypic characteristics for vaccine development. The modifications described herein that delete the C, D, and/or V ORF(s), in whole or in part, or reduce or ablate expression of the C, D, and/or V ORF(s) specify a range of desired phenotypic changes in the resulting virus or subviral particle. In preferred embodiments, C, D, and/or V deletion and knock out mutants exhibit attenuated viral growth compared to growth of a corresponding wild-type or mutant parental RSV strain. Growth, for example in cell cultures, may be reduced by about two-fold, more often about 5-fold, and preferably about 10-fold or greater overall (e.g., as measured after a 7 day period in culture) compared to growth of the corresponding wild-type or mutant parental RSV strain. In more detailed aspects, recombinant RSV of the invention exhibit altered kinetics of viral growth.

Recombinant vaccine viruses bearing the C, D, and/or V ORF deletion and knock out mutation(s) also preferably exhibit attenuation phenotypes in vivo. For example replication in the lower and/or upper respiratory tract in an accepted animal model for PIV replication in humans, e.g., hamsters and African green monkeys (AGMs), may be reduced by about two-fold, more often about 5-fold, 10-fold, or 20-fold and preferably about 100-fold to 1,000-fold or greater overall (e.g., as measured on one or each of 3 to 8 successive days following infection) compared to growth of the corresponding wild-type or mutant parental PIV strain. In addition to, or in conjunction with, the attenuation phenotypes noted above, recombinant PIV bearing C, D, and/or V ORF deletion and knock out mutation(s) may also exhibit a change in viral plaque size, a change in cytopathic effect, and/or a change in immunogenicity.

A particularly preferred characteristic of the recombinant vaccine viruses of the invention is that, while they are attenuated as noted above, they nonetheless are infectious and elicit a desired level of anti-PIV immune responsiveness in the vaccinated host. In particular, the candidate vaccine recombinants of the invention are sufficiently immunogenic that they elicit protective immune response against subsequent challenge by a wt virus. As illustrated by the examples herein, previous infection with C, D, and/or V knockout mutant viruses induced a substantial HAI antibody response to HPIV3 in both hamsters and AGMs, indicating that these exemplary recombinants are protective and therefore represent promising vaccine candidates. In other preferred vaccine recombinants of the invention, immunogenic activity will be balanced against the level of attenuation to achieve useful vaccine candidates, and will typically be marked by a reduction of replication of challenge virus, e.g., rJS HPIV3, in the lower and/or upper respiratory tract of model hosts (e.g., hamsters and non-human primates) by about 50–100-fold, 100–500-fold, preferably about 500–2,000-fold and up to 3,000-fold or greater overall (e.g., as measured between 3–8 days post-challenge). Thus, the recombinant vaccine viruses of the invention maintain immunogenicity while exhibiting concomitant reductions in replication and growth. This surprising assemblage of phenotypic traits is highly desired for vaccine development.

The instant invention provides for development of live-attenuated RSV vaccine candidates incorporating the C, D, and/or V ORF(s) deletion or knock out mutations. These recombinant viruses are constructed through a cDNA intermediate and cDNA-based recovery system. Recombinant viruses which are made from cDNA replicate independently and are propagated in the same manner as if they were biologically-derived. C, D, and/or V ORF(s) deletion and knock out mutants can be further modified to incorporate specific attenuating mutations, as well as a variety of other mutations and nucleotide modifications, to yield desired structural or phenotypic affects. Detailed descriptions of the materials and methods for producing recombinant PIV from cDNA, and for making and testing the full range of mutations and nucleotide modifications set forth herein as supplemental aspects of the present invention, provided in, e.g., Durbin et al., *Virology* 235:323–332, 1997; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference. In particular, these documents describe methods and procedures for mutagenizing, isolating and characterizing PIV to obtain attenuated mutant strains (e.g., temperature sensitive (ts), cold passaged (cp) cold-adapted (ca), small plaque (sp) and host-range restricted (hr) mutant strains) and for identifying the genetic changes that specify the attenuated phenotype. In conjunction with these methods, the foregoing documents detail procedures for determining replication, immunogenicity, genetic stability and protective efficacy of biologically derived and recombinantly produced attenuated human PIV in accepted model systems, including murine and non-human primate model systems. In addition, these documents describe general methods for developing and testing immunogenic compositions, including monovalent and bivalent vaccines, for prophylaxis and treatment of PIV infection. Methods for producing infectious recombinant PIV by construction and expression of cDNA encoding a PIV genome or antigenome coexpressed with essential PIV proteins are also described in the above-incorporated documents, which include description of the following exemplary plasmids that may be employed to produce infectious PIV viral clones: p3/7(131) (ATCC 97990); p3/7 (131)2G (ATCC 97889); and p218(131) (ATCC 97991); each deposited under the terms of the Budapest Treaty with the American Type Culture Collection (ATCC) of 10801 University Boulevard, Manassas, Va. 20110-2209, U.S.A., and granted the above identified accession numbers.

Also disclosed in the above-incorporated references are methods for constructing and evaluating infectious recombinant PIV that are modified to incorporate phenotype-specific mutations identified in biologically-derived PIV mutants, e.g., cold passaged (cp), cold adapted (ca), host range restricted (hr), small plaque (sp), and/or temperature sensitive (ts) mutants, for example the JS HPIV3 cp 45 mutant strain. Mutations identified in these mutants can be readily adopted in recombinant PIV bearing C, D, and/or V knockout mutation(s). In exemplary embodiments, one or more attenuating mutations occur in the polymerase L protein, e.g., at a position corresponding to Tyr942, Leu992, or Thr1558 of JS cp45. Preferably, these mutations are incorporated in recombinant PIV of the invention by an identical, or conservative, amino acid substitution as identified in the biological mutant. Thus, PIV recombinants may incorporate a mutation wherein $Tyr_{942}$ is replaced by His, $Leu_{992}$ is replaced by Phe, and/or $Thr_{1558}$ is replaced by Ile. Substitutions that are conservative to these replacement amino acids are also useful to achieve a desired mutant phenotype.

Other exemplary mutations adopted from a biologically derived PIV mutant include one or more mutations in the N protein, including specific mutations at a position corresponding to residues $Val_{96}$ or $Ser_{389}$ of JS cp45. In more detailed aspects, these mutations are represented as $Val_{96}$ to Ala or $Ser_{389}$ to Ala or substitutions that are conservative thereto. Also useful within recombinant PIV of the invention are amino acid substitution in the C protein, eg., a mutation at a position corresponding to $Ile_{96}$ of JS cp45, preferably represented by an identical or conservative substitution of $Ile_{96}$ to Thr. Further exemplary mutations adopted from biologically derived PIV mutants include one or more mutations in the F protein, including mutations adopted from JS cp45 at a position corresponding to residues $Ile_{420}$ or $Ala_{450}$ of JS cp45, preferably represented by acid substitutions $Ile_{420}$ to Val or $Ala_{450}$ to Thr or substitutions conservative thereto. Other PIV recombinants within the invention adopt one or more amino acid substitutions in the HN protein, as exemplified hereinbelow by a recombinant PIV adopting a mutation at a position corresponding to residue $Val_{384}$ of JS cp45, preferably represented by the substitution $Val_{384}$ to Ala.

Yet additional examples within this aspect of the invention include recombinant PIV which incorporate one or more mutations in noncoding portions of the PIV genome or antigenome, for example in a 3' leader sequence. Exemplary mutations in this context may be engineered at a position in the 3' leader of a recombinant virus at a position corresponding to nucleotide 23, 24, 28, or 45 of JS cp45. Yet additional exemplary mutations may be engineered in the N gene start sequence, for example by changing one or more nucleotides in the N gene start sequence, e.g., at a position corresponding to nucleotide 62 of JS cp45. In more detailed aspects, C, D, and/or V knockout mutants incorporate a T to C change at nucleotide 23, a C to T change at nucleotide 24, a G to T change at nucleotide 28, and/or a T to A change at nucleotide 45. Additional mutations in extragenic sequences are exemplified by a A to T change in N gene start sequence at a position corresponding to nucleotide 62 of JS.

These foregoing exemplary mutations which can be engineered in a C, D, and/or V knockout mutant have been successfully engineered and recovered in recombinant PIV—as represented by the recombinant PIV clones designated rcp45, rcp45 L, rcp45 F, rcp45 M, rcp45 HN, rcp45 C, rcp45 F, rcp45 3'N, 3'NL, and rcp45 3'NCMFHN (Durbin et al., *Virology* 235:323–332, 1997; Skiadopoulos et al., *J Virol* 72:1762–8; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference).

From JS cp45 and other biologically derived PIV mutants, a large "menu" of attenuating mutations is provided, each of which mutations can be combined with any other mutation (s) for adjusting the level of attenuation, immunogenicity and genetic stability in a recombinant PIV bearing C, D, and/or V deletion or knock out mutation(s). In this context, many recombinant PIV of the invention will include one or more, and preferably two or more, mutations from biologically derived PIV mutants, e.g., any one or combination of mutations identified in JS cp45. Preferred PIV recombinants within the invention will incorporate a plurality and up to a full complement of the mutations present in JS cp45 or other biologically derived mutant PIV strains. Preferably, these mutations are stabilized against reversion in recombinant PIV bearing C, D, and/or V deletion or knock out mutation (s) by multiple nucleotide substitutions in a codon specifying each mutation.

Yet additional mutations that may be incorporated in the C, D, and/or V ORF(s) deletion and knock out PIV mutants of the invention are mutations, e.g., attenuating mutations, identified in heterologous PIV or more distantly related nonsegmented negative stranded RNA viruses. In particular, attenuating and other desired mutations identified in one negative stranded RNA virus may be "transferred", e.g., copied, to a corresponding position within the genome or antigenome of the C, D, and/or V ORF(s) deletion and knock out mutants. Briefly, desired mutations in one heterologous negative stranded RNA virus are transferred to the PIV recipient. This involves mapping the mutation in the heterologous virus, thus identifying by sequence alignment the corresponding site in the recipient PIV, and mutating the native sequence in the RSV recipient to the mutant genotype (either by an identical or conservative mutation), as described in U.S. Provisional Application No. 60/129,006, filed by Murphy et al. on Apr. 13, 1999, incorporated herein by reference. As this disclosure teaches, it is preferable to modify the recipient genome or antigenome to encode an alteration at the subject site of mutation that corresponds conservatively to the alteration identified in the heterologous mutant virus. For example, if an amino acid substitution marks a site of mutation in the mutant virus compared to the corresponding wild-type sequence, then a similar substitution should be engineered at the corresponding residue(s) in the recombinant virus. Preferably the substitution will involve an identical or conservative amino acid to the substitute residue present in the mutant viral protein. However, it is also possible to alter the native amino acid residue at the site of mutation non-conservatively with respect to the substitute residue in the mutant protein (e.g., by using any other amino acid to disrupt or impair the function of the wild-type residue). Negative stranded RNA viruses from which exemplary mutations are identified and transferred into a recombinant PIV of the invention include other PIVs (e.g., HPIV1, HPIV2, HPIV3, BPIV or MPIV), RSV, Sendai virus (SeV), Newcastle disease virus (NDV), simian virus 5 (SV5), measles virus (MeV), rindepest virus, canine distemper virus (CDV), rabies virus (RaV), and vesicular stomatitis virus (VSV) among others. A variety of exemplary mutations are disclosed, including but not limited to an amino acid substitution of phenylalanine at position 521 of the RSV L protein corresponding to and therefore transferable to a substitution of phenylalanine (or a conservatively related amino acid) at position 456 of the HPIV3 L protein. In the case of mutations marked by deletions or insertions, these can be introduced as corresponding deletions or insertions into the recombinant virus, however the particular size and amino acid sequence of the deleted or inserted protein fragment can vary.

A variety of additional types of mutations are also disclosed in the foregoing incorporated references and can be readily engineered into a recombinant PIV of the invention to adjust growth, attenuation, immunogenicity, genetic stability or provide other advantageous structural and/or phenotypic effects. For example, restriction site markers are routinely introduced within the C, D, and/or V ORF(s) deletion or knock out mutant antigenome or genome to facilitate cDNA construction and manipulation.

Also useful within the instant invention are methods and compositions that allow production of the C, D, and/or V ORF(s) deletion and knock out mutant PIV vaccine virus as a chimeric human-bovine PIV. These recombinants are made by replacement or addition of a heterologous gene(s), genome segment(s), or single or multiple nucleotides of a human or bovine PIV to a partial or complete background bovine or human PIV genome or antigenome to produce a human-bovine chimeric PIV genome or antigenome (see, U.S. Provisional Patent Application entitled ATTENUATED HUMAN-BOVINE CHIMERIC PARAINFLUENZA VIRUS VACCINES, filed by Bailey et al. on Jul. 9, 1999 and identified by Attorney Docket No. 15280-399000US, incorporated herein by reference). In one aspect of the invention, human-bovine chimeric PIV incorporates a partial or complete bovine background PIV genome or antigenome combined with one or more heterologous gene or genome segment(s) from one or more human PIVs. Alternatively, human-bovine chimeric PIV may incorporate a partial or complete human background PIV genome or antigenome combined with a heterologous gene or genome segment from one or more bovine PIV. Genes and genome segments that are selected for use as heterologous inserts or additions to the background genome or antigenome include any wild-type or mutant genes or genome segments of N, P, C, D, V, M, F, HN, or L. In one exemplary embodiment, the ORF of the N gene of a HPIV3 recipient or background genome is substituted by the N gene ORF of BPIV3, which yielded an infectious recombinant that exhibited a host range restricted phenotype in a non-human primate host that was similar to the parental BPIV virus. Preferably, the heterologous human or bovine gene(s) encode(s) one or more of the PIV protective antigens, preferably one or more of the HN and/or F glycoproteins or an immunogenic domain or epitope thereof, although other proteins can contribute to a protective immune response and are also therefore preferred subjects for constructing human-bovine PIV chimeric viruses for use within the present invention.

Alternatively, the human-bovine chimeric PIV bearing a C, D, and/or V deletion or knock out mutation may incorporate one or more genome segment(s) encoding a cytoplasmic domain, transmembrane domain, ectodomain or immunogenic epitope of a PIV antigenic protein. These immunogenic proteins, domains and epitopes also generate novel immune responses in an immunized host. For example, addition or substitution of one or more immunogenic gene(s) or genome segment(s) from a human PIV within a bovine background genome or antigenome yields a recombinant, chimeric virus or subviral particle capable of generating an immune response directed against one or more specific human PIV "donor" strains, while the bovine backbone confers an attenuated phenotype making the chimera a useful candidate for vaccine development.

Human-bovine chimeric PIV bearing mutation(s) in the C, D, and/or V ORF(s) may be constructed by substituting the heterologous gene or genome segment for a counterpart gene or genome segment in a partial PIV background genome or antigenome. Alternatively, the heterologous gene or genome segment may be added, e.g., to a 3' or 5' non-coding region of a gene, as a supernumerary gene or genome segment in combination with a complete (or partial if another gene or genome segment is deleted) PIV background genome or antigenome. The heterologous gene or genome segment may be added at an intergenic position within a partial or complete PIV background genome or antigenome so as not to disrupt an open reading frame within the background genome or antigenome. Alternatively, the heterologous gene or genome segment may be added or substituted at a position corresponding to a wild-type gene order position of a counterpart gene or genome segment within the partial or complete PIV background genome or antigenome, which counterpart gene or genome segment is thereby replaced or displaced (e.g., to a more promoter-distal position). In yet additional embodiments, the heterologous gene or genome segment is added or substituted at a position that is more promoter-proximal or promoter-distal compared to a wild-type gene order position of the counterpart gene or genome segment within the background genome or antigenome, which enhances or reduces, respectively, expression of the heterologous gene or genome segment. These and other modifications disclosed in the cited reference are amenable to incorporation within the C, D, and/or V ORF(s) deletion and knock out mutants of the invention.

The introduction of heterologous immunogenic proteins, domains and epitopes to produce chimeric PIV is particularly useful to generate novel immune responses in an immunized host. Addition or substitution of an immunogenic gene or genome segment from one, donor PIV within a recipient genome or antigenome of a different PIV can generate an immune response directed against the donor subgroup or strain, the recipient subgroup or strain, or against both the donor and recipient subgroup or strain. To achieve this purpose, the C, D, and/or V ORF(s) deletion and knock out mutant PIV may also be constructed that express a chimeric protein, e.g., an immunogenic glycoprotein having a cytoplasmic tail and/or transmembrane domain specific to one PIV fused to an ectodomain of a different PIV to provide, e.g., a human-bovine fusion protein, or a fusion protein incorporating domains from two different human PIVs. In a preferred embodiment, a C, D, and/or V ORF(s) deletion or knock out mutant PIV genome or antigenome encodes a chimeric glycoprotein in the recombinant virus or subviral particle having both human and bovine glycoprotein domains or immunogenic epitopes. For example, a heterologous genome segment encoding a glycoprotein ectodomain from a human PIV HN or F glycoprotein may be joined with a polynucleotide sequence (i.e., a genome segment) encoding the corresponding bovine HN or F glycoprotein cytoplasmic and/or transmembrane domains to form the human-bovine chimeric PIV genome or antigenome.

In other embodiments, the C, D, and/or V ORF(s) deletion and knock out mutants useful in a vaccine formulation can be conveniently modified to accommodate antigenic drift in circulating virus. Typically the modification will be in the HN and/or F proteins. An entire HN or F gene, or a genome segment encoding a particular immunogenic region thereof, from one PIV strain is incorporated into a chimeric PIV genome or antigenome CDNA by replacement of a corresponding region in a recipient clone of a different PIV strain or subgroup, or by adding one or more copies of the gene, such that several antigenic forms are represented. Progeny virus produced from the modified PIV clone can then be used in vaccination protocols against emerging PIV strains.

Replacement of a human PIV coding sequence or non-coding sequence (e.g., a promoter, gene-end, gene-start, intergenic or other cis-acting element) with a heterologous counterpart, e.g., another human PIV or a bovine or murine PIV sequence, yields chimeric PIV having a variety of possible attenuating and other phenotypic effects. In particular, host range and other desired effects arise from substituting a bovine or murine PIV gene imported within a human PIV background, wherein the bovine or murine gene does not function efficiently in a human cell, e.g., from incompatibility of the heterologous sequence or protein with a biologically interactive human PIV sequence or protein (i.e., a sequence or protein that ordinarily cooperates with the substituted sequence or protein for viral transcription, translation, assembly, etc.) or, more typically in a host range restriction, with a cellular protein or some other aspect of the cellular milieu which is different between the permissive and less permissive host. In exemplary embodiments, bovine PIV sequences are selected for introduction into human PIV based on known aspects of bovine and human PIV structure and function.

In additional aspects of the invention, C, D, and/or V ORF(s) deletion and knock out mutant PIV are produced in which the chimeric genome or antigenome is further modified by introducing one or more mutations specifying an attenuating or other desired phenotype in the resultant chimeric virus or subviral particle. These mutations may be generated de novo and tested for attenuating effects according to a rational design mutagenesis strategy. Alternatively, the attenuating mutations may be identified in existing biologically derived mutant PIV and thereafter incorporated into C, D, and/or V ORF(s) deletion and knock out mutant PIV of the invention. These recombinant PIV offer improved characteristics of attenuation and immunogenicity for use as vaccine agents, as described above. In this context, the above-incorporated references describe construction of chimeric PIV recombinants having the HN and F genes of HPIV1 substituted into a partial HPIV3 background antigenome which is further modified to bear one or more of the attenuating mutations identified in HPIV3 JS cp45. One such chimeric recombinant incorporates all of the attenuating mutations identified in the L gene of cp45. It has since been shown that all of the cp45 mutations outside of the heterologous (HPIV1) HN and F genes can be incorporated in a HPIV3-1 recombinant to yield an attenuated, chimeric vaccine candidate.

Attenuating mutations in biologically derived PIV for incorporation within the C, D, and/or V ORF(s) deletion and knock out mutants may occur naturally or may be introduced into wild-type PIV strains by well known mutagenesis procedures. For example, incompletely attenuated parental PIV strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture, as described in the above incorporated references.

By “biologically derived PIV” is meant any PIV not produced by recombinant means. Thus, biologically derived PIV include all naturally occurring PIV, including, e.g., naturally occurring PIV having a wild-type genomic sequence and PIV having allelic or mutant genomic variations from a reference wild-type PIV sequence, e.g., PIV having a mutation specifying an attenuated phenotype. Likewise, biologically derived PIV include PIV mutants derived from a parental PIV by, inter alia, artificial mutagenesis and selection procedures.

As noted above, production of a sufficiently attenuated biologically derived PIV mutant can be accomplished by several known methods. One such procedure involves subjecting a partially attenuated virus to passage in cell culture at progressively lower, attenuating temperatures. For example, partially attenuated mutants are produced by passage in cell cultures at suboptimal temperatures. Thus, a cp mutant or other partially attenuated PIV strain is adapted to efficient growth at a lower temperature by passage in culture. This selection of mutant PIV during cold-passage substantially reduces any residual virulence in the derivative strains as compared to the partially attenuated parent.

Alternatively, specific mutations can be introduced into biologically derived PIV by subjecting a partially attenuated parent virus to chemical mutagenesis, e.g., to introduce ts mutations or, in the case of viruses which are already ts, additional ts mutations sufficient to confer increased attenuation and/or stability of the ts phenotype of the attenuated derivative. Means for the introduction of ts mutations into PIV include replication of the virus in the presence of a mutagen such as 5-fluorouridine according to generally known procedures. Other chemical mutagens can also be used. Attenuation can result from a ts mutation in almost any PIV gene, although a particularly amenable target for this purpose has been found to be the polymerase (L) gene.

The level of temperature sensitivity of replication in exemplary attenuated PIV for use within the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of PIV correlate with the mutant's shutoff temperature.

The JS cp45 HPIV3 mutant has been found to be relatively stable genetically, highly immunogenic, and satisfactorily attenuated. Nucleotide sequence analysis of this biologically derived and recombinant viruses incorporating various individual and combined mutations found therein, indicates that each level of increased attenuation is associated with specific nucleotide and amino acid substitutions. The above-incorporated references also disclose how to routinely distinguish between silent incidental mutations and those responsible for phenotype differences by introducing the mutations, separately and in various combinations, into the genome or antigenome of infectious PIV clones. This process coupled with evaluation of phenotype characteristics of parental and derivative virus identifies mutations responsible for such desired characteristics as attenuation, temperature sensitivity, cold-adaptation, small plaque size, host range restriction, etc.

Mutations thus identified are compiled into a "menu" and are then introduced as desired, singly or in combination, to adjust a C, D, and/or V ORF(s) deletion or knock out mutant to an appropriate level of attenuation, immunogenicity, genetic resistance to reversion from an attenuated phenotype, etc., as desired. In accordance with the foregoing description, the ability to produce infectious PIV from cDNA permits introduction of specific engineered changes within the C, D, and/or V ORF(s) deletion and knock out mutants. In particular, infectious, recombinant PIV are employed for identification of specific mutation(s) in biologically derived, attenuated PIV strains, for example mutations which specify ts, ca, att and other phenotypes. Desired mutations are thus identified and introduced into recombinant, the C, D, and/or V ORF(s) deletion and knock out mutant PIV vaccine strains. The capability of producing virus from cDNA allows for routine incorporation of these mutations, individually or in various selected combinations, into a fill-length cDNA clone, whereafter the phenotypes of rescued recombinant viruses containing the introduced mutations to be readily determined.

By identifying and incorporating specific, biologically derived mutations associated with desired phenotypes, e.g., a cp or ts phenotype, into infectious PIV clones, the invention provides for other, site-specific modifications at, or within close proximity to, the identified mutation. Whereas most attenuating mutations produced in biologically derived PIV are single nucleotide changes, other "site specific" mutations can also be incorporated by recombinant techniques into biologically derived or recombinant PIV. As used herein, site-specific mutations include insertions, substitutions, deletions or rearrangements of from 1 to 3, up to about 5–15 or more altered nucleotides (e.g., altered from a wild-type PIV sequence, from a sequence of a selected mutant PIV strain, or from a parent recombinant PIV clone subjected to mutagenesis). Such site-specific mutations may be incorporated at, or within the region of, a selected, biologically derived point mutation. Alternatively, the mutations can be introduced in various other contexts within a PIV clone, for example at or near a cis-acting regulatory sequence or nucleotide sequence encoding a protein active site, binding site, immunogenic epitope, etc. Site-specific PIV mutants typically retain a desired attenuating phenotype, but may additionally exhibit altered phenotypic characteristics unrelated to attenuation, e.g., enhanced or broadened immunogenicity, and/or improved growth. Further examples of desired, site-specific mutants include recombinant PIV designed to incorporate additional, stabilizing nucleotide mutations in a codon specifying an attenuating point mutation. Where possible, two or more nucleotide substitutions are introduced at codons that specify attenuating amino acid changes in a parent mutant or recombinant PIV clone, yielding a biologically derived or recombinant PIV having genetic resistance to reversion from an attenuated phenotype. In other embodiments, site-specific nucleotide substitutions, additions, deletions or rearrangements are introduced upstream (N-terminal direction) or downstream (C-terminal direction), e.g, from 1 to 3, 5–10 and up to 15 nucleotides or more 5' or 3', relative to a targeted nucleotide position, e.g., to construct or ablate an existing cis-acting regulatory element.

In addition to single and multiple point mutations and site-specific mutations, changes to the C, D, and/or V ORF(s) deletion and knock out mutant PIV disclosed herein include deletions, insertions, substitutions or rearrangements of whole genes or genome segments outside of the deleted or ablated C, D, and/or V ORF(s) or genome segments. These mutations may alter small numbers of bases (e.g., from 15–30 bases, up to 35–50 bases or more), large blocks of nucleotides (e.g., 50–100, 100–300, 300–500, 500–1,000 bases), or nearly complete or complete genes (e.g., 1,000–1,500 nucleotides, 1,500–2,500 nucleotides, 2,500–5,000, nucleotides, 5,00–6,5000 nucleotides or more) in the donor or recipient genome or antigenome, depending upon the nature of the change (i.e., a small number of bases may be changed to insert or ablate an immunogenic epitope or change a small genome segment, whereas large block(s) of bases are involved when genes or large genome segments are added, substituted, deleted or rearranged.

In additional aspects, the invention provides for supplementation of mutations adopted into a recombinant PIV clone from biologically derived PIV, e.g., cp and ts mutations, with additional types of mutations involving the same or different genes in a further modified PIV clone. Each of the PIV genes can be selectively altered in terms of expression levels, or can be added deleted, substituted or rearranged, in whole or in part, alone or in combination with other desired modifications, to yield a C, D, and/or V ORF(s) deletion or knock out mutant PIV exhibiting novel vaccine characteristics. Thus, in addition to or in combination with attenuating mutations adopted from biologically derived PIV mutants, the present invention also provides a range of additional methods for attenuating or otherwise modifying the phenotype of the C, D, and/or V ORF(s) deletion and knock out mutant PIV based on recombinant engineering of infectious PIV clones. A variety of alterations can be produced in an isolated polynucleotide sequence encoding a targeted gene or genome segment, including a donor or recipient gene or genome segment in a chimeric PIV genome or antigenome for incorporation into infectious clones. More specifically, to achieve desired structural and phenotypic changes in recombinant PIV, the invention allows for introduction of modifications which delete, substitute, introduce, or rearrange a selected nucleotide or plurality of nucleotides from a parent genome or antigenome, as well as mutations which delete, substitute, introduce or rearrange whole gene(s) or genome segment(s), within a C, D, and/or V ORF(s) deletion or knock out mutant PIV clone.

Thus provided are modifications in the C, D, and/or V ORF(s) deletion and knock out mutant PIV which simply alter or ablate expression of a selected gene in addition to the deleted or ablated the C, D, and/or V ORF(s) or genome segment(s), e.g., by introducing a termination codon within a selected PIV coding sequence, changing the position of a PIV gene relative to an operably linked promoter, introducing an upstream start codon to alter rates of expression, modifying (e.g., by changing position, altering an existing sequence, or substituting an existing sequence with a heterologous sequence) GS and/or GE transcription signals to alter phenotype (e.g., growth, temperature restrictions on transcription, etc.), and various other deletions, substitutions, additions and rearrangements that specify quantitative or qualitative changes in viral replication, transcription of selected gene(s), or translation of selected protein(s). In this context, any PIV gene which is not essential for growth can be ablated or otherwise modified in a recombinant PIV to yield desired effects on virulence, pathogenesis, immunogenicity and other phenotypic characters.

In addition, a variety of other genetic alterations can be produced in a PIV genome or antigenome for incorporation into human-bovine chimeric PIV, alone or together with one or more attenuating mutations adopted from a biologically derived mutant PIV, e.g., to adjust growth, attenuation, immunogenicity, genetic stability or provide other advantageous structural and/or phenotypic effects. These additional types of mutations are also disclosed in the foregoing incorporated references and can be readily engineered into human-bovine chimeric PIV of the invention. For example, restriction site markers are routinely introduced within the human-bovine chimeric PIV antigenome or genome to facilitate cDNA construction and manipulation.

Also provided within the invention are genetic modifications in a C, D, and/or V ORF(s) deletion or knock out mutant PIV which alter or ablate the expression of a selected gene or genome segment outside of the targeted the C, D, and/or V ORF(s) without removing the gene or genome segment from the PIV clone. For example, this can be achieved by introducing a mutation that changes the coding assignment of an initiation codon or introduces a termination codon within a selected coding sequence, changing the position of a gene or introducing an upstream start codon to alter its rate of expression, or changing GS and/or GE transcription signals to alter phenotype (e.g., growth, temperature restrictions on transcription, etc.). In more detailed aspects of the invention, the C, D, and/or V ORF(s) deletion and knock out mutant PIV are provided in which expression of a gene outside the targeted C, D, and/or V ORF(s) is ablated at the translational level without deletion of the gene or of a segment thereof, by, e.g., introducing multiple translational termination codons into a translational open reading frame (ORF). This yields viable virus in which a selected gene has been silenced at the level of translation without deleting its gene. In other embodiments, multiple stop codons are introduced in the targeted ORF(s). Alternatively a mutation is introduced in an RNA editing site, or a mutation is introduced that alters the amino acid specified by an initiation codon. These forms of knock out virus will often exhibit reduced growth rates and small plaque sizes in tissue culture. Thus, these methods provide yet additional, novel types of attenuating mutations which ablate expression of a viral gene that is not one of the major viral protective antigens. In this context, knock out virus phenotypes produced without deletion of a gene or genome segment can be alternatively produced by deletion mutagenesis, as described herein, to effectively preclude correcting mutations that may restore synthesis of a target protein. Several other gene knock outs for the C, D, and/or V ORF(s) deletion and knock out mutants can be made using alternate designs and methods that are well known in the art (as described, for example, in (Kretschmer et al., *Virology* 216:309–316, 1996; Radicle et al., *Virology* 217:418–412, 1996; and Kato et al., *EMBOSS J.* 16:178–587, 1987; and Schneider et al., *Virology* 277:314–322, 1996, each incorporated herein by reference).

Other mutations for incorporation into the C, D, and/or V ORF(s) deletion and knock out mutant PIV of the invention include mutations directed toward cis-acting signals, which can be identified, e.g., by mutational analysis of PIV minigenomes. For example, insertional and deletional analysis of the leader and trailer and flanking sequences identifies viral promoters and transcription signals and provides a series of mutations associated with varying degrees of reduction of RNA replication or transcription. Saturation mutagenesis (whereby each position in turn is modified to each of the nucleotide alternatives) of these cis-acting signals also has identified many mutations which reduced (or in one case increased) RNA replication or transcription. Any of these mutations can be inserted into a C, D, and/or V ORF(s) deletion or knock out mutant PIV antigenome or genome as described herein. Evaluation and manipulation of trans-acting proteins and cis-acting RNA sequences using the complete antigenome cDNA is assisted by the use of PIV minigenomes as described in the above-incorporated references.

Additional mutations within the C, D, and/or V ORF(s) deletion and knock out mutant PIV involve replacement of the 3' end of genome with its counterpart from antigenome, which is associated with changes in RNA replication and transcription. In one exemplary embodiment, the level of expression of specific PIV proteins, such as the protective HN and/or F antigens, can be increased by substituting the natural sequences with ones which have been made synthetically and designed to be consistent with efficient translation. In this context, it has been shown that codon usage can be a major factor in the level of translation of mammalian viral proteins (Haas et al., *Current Biol.* 6:315–324, 1996, incorporated herein by reference). Examination of the codon usage of the mRNAs encoding the HN and F proteins of PIV, which are the major protective antigens, will provide for improvement of codon usage by recombinant methods to achieve improved expression for these genes.

In another exemplary embodiment, a sequence surrounding a translational start site (preferably including a nucleotide in the −3 position) of a selected PIV gene is modified, alone or in combination with introduction of an upstream start codon, to modulate PIV gene expression by specifying up- or down-regulation of translation. Alternatively, or in combination with other PIV modifications disclosed herein, the C, D, and/or V ORF(s) deletion and knock out mutant PIV gene expression can be modulated by altering a transcriptional GS or GE signal of any selected gene(s) of the virus. In alternative embodiments, levels of gene expression in the C, D, and/or V ORF(s) deletion and knock out mutants are modified at the level of transcription. In one aspect, the position of a selected gene in the PIV gene map can be changed to a more promoter-proximal or promoter-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels often attended by a commensurate decrease in expression levels for reciprocally, positionally substituted genes. These and other transpositioning changes yield novel C, D, and/or V ORF(s) deletion and knock out mutants of PIV having attenuated phenotypes, for example due to decreased expression of selected viral proteins involved in RNA replication, or having other desirable properties such as increased antigen expression.

Infectious C, D, and/or V ORF(s) deletion and knock out mutant PIV clones of the invention can also be engineered according to the methods and compositions disclosed herein to enhance immunogenicity and induce a level of protection greater than that provided by infection with a wild-type PIV or a parent PIV. For example, an immunogenic epitope from a heterologous PIV strain or type, or from a non-PIV source such as RSV, can be added to a recombinant clone by appropriate nucleotide changes in the polynucleotide sequence encoding the genome or antigenome. Alternatively, mutant PIV of the invention can be engineered to add or ablate (e.g., by amino acid insertion, substitution or deletion) immunogenic proteins, protein domains, or forms of specific proteins associated with desirable or undesirable immunological reactions.

Within the methods of the invention, additional genes or genome segments may be inserted into or proximate to the C, D, and/or V ORF(s) deletion and knock out mutant PIV genome or antigenome. These genes may be under common control with recipient genes, or may be under the control of an independent set of transcription signals. Genes of interest include the PIV genes identified above, as well as non-PIV genes. Non-PIV genes of interest include those encoding cytokines (e.g., IL-2 through IL-18, especially IL-2, IL-6 and IL-12, IL-18, etc.), gamma-interferon, and proteins rich in T helper cell epitopes. These additional proteins can be expressed either as a separate protein, or as a supernumerary copy of an existing PIV proteins, such as HN or F. This provides the ability to modify and improve the immune responses against PIV both quantitatively and qualitatively.

Deletions, insertions, substitutions and other mutations involving changes of whole viral genes or genome segments within a C, D, and/or V ORF(s) deletion or knock out mutant yield highly stable vaccine candidates, which are particularly important in the case of immunosuppressed individuals. Many of these changes will result in attenuation of resultant vaccine strains, whereas others will specify different types of desired phenotypic changes. For example, accessory (i.e., not essential for in vitro growth) genes are excellent candidates to encode proteins that specifically interfere with host immunity (see, e.g., Kato et al., *EMBO. J.* 16:578–87, 1997, incorporated herein by reference). Ablation of such genes in vaccine viruses is expected to reduce virulence and pathogenesis and/or improve immunogenicity.

In more detailed aspects of the invention, the C, D, and/or V ORF(s) deletion and knock out mutants are employed as vectors for protective antigens of other pathogens, particularly respiratory tract pathogens such as RSV. For example, recombinant PIV may be engineered which incorporate sequences that encode protective antigens from RSV to produce infectious, attenuated vaccine virus. The cloning of RSV cDNA and other disclosure is provided in U.S. Provisional Patent Application No. 60/007,083, filed Sep. 27, 1995; U.S. patent application Ser. No. 08/720,132, filed Sep.27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. patent application Ser. No. 08/892,403, filed Jul. 15, 1997 (corresponding to International Publication No. WO 98/02530); U.S. patent application Ser. No. 09/291,894, filed by Collins et al. on Apr. 13, 1999, and its successor PCT application published as WO 00/61611 on Oct. 19, 2000; U.S. Provisional Application No. 60/129,006, filed by Murphy et al. on Apr. 13, 1999; Collins, et al., *Proc Nat. Acad. Sci. USA* 92:11563–11567, 1995; Bukreyev, et al., *J Virol* 70:6634–41, 1996, Juhasz et al., *J. Virol.* 71(8):5814–5819, 1997; Durbin et al., *Virology* 235:323–332, 1997; He et al. *Virology* 237:249–260, 1997; Baron et al. *J. Virol.* 71:1265–1271, 1997; Whitehead et al., *Virology* 247(2):232–9, 1998a; Whitehead et al., *J. Virol.* 72(5):4467–4471, 1998b; Jin et al. *Virology* 251:206–214, 1998; and Whitehead et al., *J. Virol.* 73:(4)3438–3442, 1999, and Bukreyev, et al., *Proc Nat Acad Sci USA* 96:2367–72, 1999, each incorporated herein by reference in its entirety for all purposes).

According to this aspect of the invention, C, D, and/or V ORF(s) deletion and knock out mutant PIV are provided which incorporate at least one RSV sequence. For example, individual genes of HPIV3 may be replaced with counterpart genes from human RSV. Alternatively, a selected, heterologous genome segment, e.g. encoding a cytoplasmic tail, transmembrane domain or ectodomain of an RSV glycoprotein, is substituted for a counterpart genome segment in, e.g., the same gene in HPIV3 or within a different gene in HPIV3, or added within a non-coding sequence of the HPIV3 genome or antigenome to yield a chimeric PIV-RSV glycoprotein. In one embodiment, a genome segment from an F gene of human RSV is substituted for a counterpart HPIV3 genome segment to yield constructs encoding chimeric proteins, e.g. fusion proteins having a cytoplasmic tail and/or transmembrane domain of PIV fused to an ectodomain of RSV to yield a novel attenuated virus, and/or a multivalent vaccine immunogenic against both PIV and RSV.

In addition to the above described modifications to C, D, and/or V deletion or knock out mutants, different or additional modifications in PIV clones can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

In another aspect of the invention, compositions (e.g., isolated polynucleotides and vectors incorporating human-bovine chimeric PIV-encoding CDNA) are provided for producing an isolated infectious PIV. Using these compositions and methods, infectious PIVs are generated from a PIV genome or antigenome, a nucleocapsid (N) protein, a nucleocapsid phosphoprotein (P), and a large (L) polymerase protein. In related aspects of the invention, compositions and methods are provided for introducing the aforementioned structural and phenotypic changes into a recombinant PIV to yield infectious, attenuated vaccine viruses.

Introduction of the foregoing defined mutations into an infectious, C, D, and/or V deletion or knock out mutant clone can be achieved by a variety of well known methods. By "infectious clone" with regard to DNA is meant cDNA or its product, synthetic or otherwise, which can be transcribed into genomic or antigenomic RNA capable of serving as template to produce the genome of an infectious virus or subviral particle. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA as described herein has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. This can be through the intermediate of a single-stranded phagemid form, such as using the Muta-gene® kit of Bio-Rad Laboratories (Richmond, Calif.) or a method using a double-stranded plasmid directly as template such as the Chameleon mutagenesis kit of Stratagene (La Jolla, Calif.), or by the polymerase chain reaction employing either an oligonucleotide primer or template which contains the mutation(s) of interest. A mutated subfragment can then be assembled into the complete antigenome or genome cDNA. A variety of other mutagenesis techniques are known and available for use in producing the mutations of interest in the PIV antigenome or genome cDNA. Mutations can vary from single nucleotide changes to replacement of large cDNA pieces containing one or more genes or genome regions.

Thus, in one illustrative embodiment mutations are introduced by using the Muta-gene phagemid in vitro mutagenesis kit available from Bio-Rad. In brief, cDNA encoding a portion of a PIV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome fragment is then amplified and the mutated piece is then reintroduced into the full-length genome or antigenome clone.

The invention also provides methods for producing infectious human-bovine chimeric PIV from one or more isolated polynucleotides, e.g., one or more cDNAs. According to the present invention cDNA encoding a PIV genome or antigenome is constructed for intracellular or in vitro coexpression with the necessary viral proteins to form infectious PIV. By "PIV antigenome" is meant an isolated positive-sense polynucleotide molecule which serves as the template for the synthesis of progeny PIV genome. Preferably a cDNA is constructed which is a positive-sense version of the PIV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, and L proteins.

For purposes of the present invention the genome or antigenome of the recombinant PIV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule, or can be expressed directly from the genome or antigenome cDNA.

By recombinant PIV is meant a PIV or PIV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in PIV gene expression, for example, a promoter, a structural or coding sequence which is transcribed into PIV RNA, and appropriate transcription initiation and termination sequences.

To produce infectious PIV from cDNA-expressed genome or antigenome, the genome or antigenome is coexpressed with those PIV proteins necessary to (i) produce a nucleocapsid capable of RNA replication, and (ii) render progeny nucleocapsids competent for both RNA replication and transcription. Transcription by the genome nucleocapsid provides the other PIV proteins and initiates a productive infection. Alternatively, additional PIV proteins needed for a productive infection can be supplied by coexpression.

Infectious PIV of the invention are produced by intracellular or cell-free coexpression of one or more isolated polynucleotide molecules that encode a PIV genome or antigenome RNA, together with one or more polynucleotides encoding viral proteins necessary to generate a transcribing, replicating nucleocapsid. Among the viral proteins useful for coexpression to yield infectious PIV are the major nucleocapsid protein (N) protein, nucleocapsid phosphoprotein (P), large (L) polymerase protein, fusion protein (F), hemagglutinin-neuraminidase glycoprotein (HN), and matrix (M) protein. Also useful in this context are products of the C, D and V ORFs of PIV.

cDNAs encoding a PIV genome or antigenome are constructed for intracellular or in vitro coexpression with the necessary viral proteins to form infectious PIV. By "PIV antigenome" is meant an isolated positive-sense polynucleotide molecule which serves as a template for synthesis of progeny PIV genome. Preferably a cDNA is constructed which is a positive-sense version of the PIV genome corresponding to the replicative intermediate RNA, or antigenome, so as to minimize the possibility of hybridizing with positive-sense transcripts of complementing sequences encoding proteins necessary to generate a transcribing, replicating nucleocapsid.

In some embodiments of the invention the genome or antigenome of a recombinant PIV (rPIV) need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule. In other embodiments, the PIV genome or antigenome encodes all functions necessary for viral growth, replication, and infection without the participation of a helper virus or viral function provided by a plasmid or helper cell line.

By "recombinant PIV" is meant a PIV or PIV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in PIV gene expression, for example, a promoter, a structural or coding sequence which is transcribed into PIV RNA, and appropriate transcription initiation and termination sequences.

To produce infectious PIV from a cDNA-expressed PIV genome or antigenome, the genome or antigenome is coexpressed with those PIV N, P and L proteins necessary to (i) produce a nucleocapsid capable of RNA replication, and (ii) render progeny nucleocapsids competent for both RNA replication and transcription. Transcription by the genome nucleocapsid provides the other PIV proteins and initiates a productive infection. Alternatively, additional PIV proteins needed for a productive infection can be supplied by coexpression.

Synthesis of PIV antigenome or genome together with the above-mentioned viral proteins can also be achieved in vitro (cell-free), e.g., using a combined transcription-translation reaction, followed by transfection into cells. Alternatively, antigenome or genome RNA can be synthesized in vitro and transfected into cells expressing PIV proteins.

In certain embodiments of the invention, complementing sequences encoding proteins necessary to generate a transcribing, replicating PIV nucleocapsid are provided by one or more helper viruses. Such helper viruses can be wild type or mutant. Preferably, the helper virus can be distinguished phenotypically from the virus encoded by the PIV cDNA. For example, it is desirable to provide monoclonal antibodies which react immunologically with the helper virus but not the virus encoded by the PIV cDNA. Such antibodies can be neutralizing antibodies. In some embodiments, the antibodies can be used in affinity chromatography to separate the helper virus from the recombinant virus. To aid the procurement of such antibodies, mutations can be introduced into the PIV cDNA to provide antigenic diversity from the helper virus, such as in the HN or F glycoprotein genes.

In alternate embodiments of the invention, the N, P, L and other desired PIV proteins are encoded by one or more non-viral expression vectors, which can be the same or separate from that which encodes the genome or antigenome. Additional proteins may be included as desired, each encoded by its own vector or by a vector encoding one or more of the N, P, L and other desired PIV proteins, or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., *Virology,* 210: 202–205 (1995), incorporated herein by reference in its entirety). The viral proteins, and/or T7 RNA polymerase, can also be provided by transformed mammalian cells or by transfection of preformed mRNA or protein.

A PIV antigenome may be constructed for use in the present invention by, e.g., assembling cloned cDNA segments, representing in aggregate the complete antigenome, by polymerase chain reaction or the like (PCR; described in, e.g., U.S. Pat. Nos. 4,683,195 and 4,683,202, and *PCR Protocols: A Guide to Methods and Applications,* Innis et al., eds., Academic Press, San Diego (1990), each incorporated herein by reference in its entirety) of reverse-transcribed copies of PIV mRNA or genome RNA. For example, a first construct is generated which comprises cDNAs containing the left hand end of the antigenome, spanning from an appropriate-promoter (e.g., T7 RNA polymerase promoter) and assembled in an appropriate expression vector, such as a plasmid, cosmid, phage, or DNA virus vector. The vector may be modified by mutagenesis and/or insertion of synthetic polylinker containing unique restriction sites designed to facilitate assembly. For ease of preparation the N, P, L and other desired PIV proteins can be assembled in one or more separate vectors. The right hand end of the antigenome plasmid may contain additional sequences as desired, such as a flanking ribozyme and tandem T7 transcriptional terminators. The ribozyme can be hammerhead type (e.g., Grosfeld et al., (1995), supra), which would yield a 3' end containing a single nonviral nucleotide, or can be any of the other suitable ribozymes such as that of hepatitis delta virus (Perrotta et al., *Nature* 350:434–436 (1991), incorporated herein by reference in its entirety) which would yield a 3' end free of non-PIV nucleotides. The left- and right-hand ends are then joined via a common restriction site.

A variety of nucleotide insertions, deletions and rearrangements can be made in the PIV genome or antigenome during or after construction of the cDNA. For example, specific desired nucleotide sequences can be synthesized and inserted at appropriate regions in the cDNA using convenient restriction enzyme sites. Alternatively, such techniques as site-specific mutagenesis, alanine scanning, PCR mutagenesis, or other such techniques well known in the art can be used to introduce mutations into the cDNA.

Alternative means to construct cDNA encoding the genome or antigenome include reverse transcription-PCR using improved PCR conditions (e.g., as described in Cheng et al., *Proc. Natl. Acad. Sci. USA* 91:5695–5699 (1994)), incorporated herein by reference) to reduce the number of subunit cDNA components to as few as one or two pieces. In other embodiments different promoters can be used (e.g., T3, SP6) or different ribozymes (e.g., that of hepatitis delta virus). Different DNA vectors (e.g., cosmids) can be used for propagation to better accommodate the larger size genome or antigenome.

Isolated polynucleotides (e.g., cDNA) encoding the genome or antigenome may be inserted into appropriate host cells by transfection, electroporation, mechanical insertion, transduction or the like, into cells which are capable of supporting a productive PIV infection, e.g., HEp-2, FRhL-DBS2, LLC-MK2, MRC-5, and Vero cells. Transfection of isolated polynucleotide sequences may be introduced into cultured cells by, for example, calcium phosphate-mediated transfection (Wigler et al., *Cell* 14: 725 (1978); Corsaro and Pearson, Somatic Cell Genetics 7: 603 (1981); Graham and Van der Eb, *Virology* 52: 456 (1973)), electroporation (Neumann et al., *EMBO J.* 1: 841–845 (1982)), DEAE-dextran mediated transfection (Ausubel et al., (ed.) *Current Protocols in Molecular Biology,* John Wiley and Sons, Inc., NY (1987), cationic lipid-mediated transfection (Hawley-Nelson et al., *Focus* 15: 73–79 (1993)) or a commercially available transfection regent, e.g., LipofectACE® (Life Technologies, Gaithersburg, Md.) or the like (each of the foregoing references are incorporated herein by reference in its entirety).

As noted above, in some embodiments of the invention the N, P, L and other desired PIV proteins are encoded by one or more helper viruses which is phenotypically distinguishable from that which encodes the genome or antigenome. The N, P, L and other desired PIV proteins can also be encoded by one or more expression vectors which can be the same or separate from that which encodes the genome or antigenome, and various combinations thereof. Additional proteins may be included as desired, encoded by its own vector or by a vector encoding one or more of the N, P, L and other desired PIV proteins, or the complete genome or antigenome.

By providing infectious clones of PIV the invention permits a wide range of alterations to be recombinantly produced within the PIV genome (or antigenome), yielding defined mutations which specify desired phenotypic changes. By "infectious clone" is meant cDNA or its product, synthetic or otherwise, RNA capable of being directly incorporated into infectious virions which can be transcribed into genomic or antigenomic RNA capable of serving as a template to produce the genome of infectious viral or subviral particles. As noted above, defmed mutations can be introduced by a variety of conventional techniques (e.g., site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA subjects provide for better ease of manipulation than large cDNA subjects, and then readily assembled into a complete cDNA. Thus, the complete antigenome or genome cDNA, or a selected subfragment thereof, can be used as a template for oligonucleotide-directed mutagenesis. This can be through the intermediate of a single-stranded phagemid form, such as using the MUTA-gen® kit of Bio-Rad Laboratories (Richmond, Calif.), or a method using the double-stranded plasmid directly as a template such as the Chameleon® mutagenesis kit of Strategene (La Jolla, Calif.), or by the polymerase chain reaction employing either an oligonucleotide primer or a template which contains the mutation (s) of interest. A mutated subfragment can then be assembled into the complete antigenome or genome cDNA. A variety of other mutagenesis techniques are known and can be routinely adapted for use in producing the mutations of interest in a PIV antigenome or genome cDNA of the invention.

Thus, in one illustrative embodiment mutations are introduced by using the MUTA-gene® phagemid in vitro mutagenesis kit available from Bio-Rad Laboratories. In brief, cDNA encoding an PIV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome is then amplified.

Mutations can vary from single nucleotide changes to the introduction, deletion or replacement of large cDNA segments containing one or more genes or genome segments. Genome segments can correspond to structural and/or functional domains, e.g., cytoplasmic, transmembrane or ectodomains of proteins, active sites such as sites that mediate binding or other biochemical interactions with different proteins, epitopic sites, e.g., sites that stimulate antibody binding and/or humoral or cell mediated immune responses, etc. Useful genome segments in this regard range from about 15–35 nucleotides in the case of genome segments encoding small functional domains of proteins, e.g., epitopic sites, to about 50, 75, 100, 200–500, and 500–1,500 or more nucleotides.

The ability to introduce defined mutations into infectious PIV has many applications, including the manipulation of PIV pathogenic and immunogenic mechanisms. For example, the functions of PIV proteins, including the N, P, M, F, HN, and L proteins and C, D and V ORF products, can be manipulated by introducing mutations which ablate or reduce the level of protein expression, or which yield mutant protein. Various genome RNA structural features, such as promoters, intergenic regions, and transcription signals, can also be routinely manipulated within the methods and compositions of the invention. The effects of trans-acting proteins and cis-acting RNA sequences can be readily determined, for example, using a complete antigenome cDNA in parallel assays employing PIV minigenomes (Dimock, et al., *J. Virol.* 67: 2772–8 (1993), incorporated herein by reference in its entirety), whose rescue-dependent status is useful in characterizing those mutants that may be too inhibitory to be recovered in replication-independent infectious virus.

Certain substitutions, insertions, deletions or rearrangements of genes or gene segments within recombinant PIV of the invention (e.g., substitutions of a gene segment encoding a selected protein or protein region, for instance a cytoplasmic tail, transmembrane domain or ectodomain, an epitopic site or region, a binding site or region, an active site or region containing an active site, etc.) are made in structural or functional relation to an existing, "counterpart" gene or gene segment from the same or different PIV or other source. Such modifications yield novel recombinants having desired phenotypic changes compared to wild-type or parental PIV or other viral strains. For example, recombinants of this type may express a chimeric protein having a cytoplasmic tail and/or transmembrane domain of one PIV fused to an ectodomain of another PIV. Other exemplary recombinants of this type express duplicate protein regions, such as duplicate immunogenic regions.

As used herein, "counterpart" genes, gene segments, proteins or protein regions, are typically from heterologous sources (e.g., from different PIV genes, or representing the same (i.e., homologous or allelic) gene or gene segment in different PIV types or strains). Typical counterparts selected in this context share gross structural features, e.g., each counterpart may encode a comparable protein or protein structural domain, such as a cytoplasmic domain, transmembrane domain, ectodomain, binding site or region, epitopic site or region, etc. Counterpart domains and their encoding gene segments embrace an assemblage of species having a range of size and sequence variations defined by a common biological activity among the domain or gene segment variants.

Counterpart genes and gene segments, as well as other polynucleotides disclosed herein for producing recombinant PIV within the invention, often share substantial sequence identity with a selected polynucleotide "reference sequence," e.g., with another selected counterpart sequence. As used herein, a "reference sequence" is a defined sequence used as a basis for sequence comparison, for example, a segment of a full-length cDNA or gene, or a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988) (each of which is incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

In addition to these polynucleotide sequence relationships, proteins and protein regions encoded by recombinant PIV of the invention are also typically selected to have conservative relationships, i.e. to have substantial sequence identity or sequence similarity, with selected reference polypeptides. As applied to polypeptides, the term "sequence identity" means peptides share identical amino acids at corresponding positions. The term "sequence similarity" means peptides have identical or similar amino acids (i.e., conservative substitutions) at corresponding positions. The term "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). The term "substantial similarity" means that two peptide sequences share corresponding percentages of sequence similarity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Abbreviations for the twenty naturally occurring amino acids used herein follow conventional usage (Immunology—A Synthesis (2nd ed., E. S. Golub & D. R. Gren, eds., Sinauer Associates, Sunderland, Mass., 1991), incorporated herein by reference). Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and imino acids (e.g., 4-hydroxyproline). Moreover, amino acids may be modified by glycosylation, phosphorylation and the like.

To select candidate vaccine viruses according to the invention, the criteria of viability, attenuation and immunogenicity are determined according to well known methods. Viruses which will be most desired in vaccines of the invention must maintain viability, have a stable attenuation phenotype, exhibit replication in an immunized host (albeit at lower levels), and effectively elicit production of an immune response in a vaccinee sufficient to confer protection against serious disease caused by subsequent infection from wild-type virus. The recombinant PIV of the invention are not only viable and more appropriately attenuated than previous vaccine candidates, but are more stable genetically in vivo—retaining the ability to stimulate a protective immune response and in some instances to expand the protection afforded by multiple modifications, e.g., induce protection against different viral strains or subgroups, or protection by a different immunologic basis, e.g., secretory versus serum immunoglobulins, cellular immunity, and the like.

Recombinant PIV of the invention can be tested in various well known and generally accepted in vitro and in vivo models to confirm adequate attenuation, resistance to phenotypic reversion, and immunogenicity for vaccine use. In in vitro assays, the modified virus (e.g., a multiply attenuated, biologically derived or recombinant PIV) is tested, e.g., for temperature sensitivity of virus replication, i.e. ts phenotype, and for the small plaque or other desired phenotype. Modified viruses are further tested in animal models of PIV infection. A variety of animal models have been described and are summarized in various references incorporated herein. PIV model systems, including rodents and non-human primates, for evaluating attenuation and immunogenic activity of PIV vaccine candidates are widely accepted in the art, and the data obtained therefrom correlate well with PIV infection, attenuation and immunogenicity in humans.

In accordance with the foregoing description, the invention also provides isolated, infectious recombinant PIV viral compositions for vaccine use. The attenuated virus which is a component of a vaccine is in an isolated and typically purified form. By isolated is meant to refer to PIV which is in other than a native environment of a wild-type virus, such as the nasopharynx of an infected individual. More generally, isolated is meant to include the attenuated virus as a component of a cell culture or other artificial medium where it can be propagated and characterized in a controlled setting. For example, attenuated PIV of the invention may be produced by an infected cell culture, separated from the cell culture and added to a stabilizer.

For vaccine use, recombinant PIV produced according to the present invention can be used directly in vaccine formulations, or lyophilized, as desired, using lyophilization protocols well known to the artisan. Lyophilized virus will typically be maintained at about 4° C. When ready for use the lyophilized virus is reconstituted in a stabilizing solution, e.g., saline, SPG, $Mg^{++}$ and HEPES, with or without adjuvant, as further described below.

PIV vaccines of the invention contain as an active ingredient an immunogenically effective amount of PIV produced as described herein. The modified virus may be introduced into a host with a physiologically acceptable carrier and/or adjuvant. Useful carriers are well known in the art, and include, e.g., water, buffered w water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, MPL™ (3-o-deacylated monophosphoryl lipid A; RIBI ImmunoChem Research, Inc., Hamilton, Mont.) and IL-12 (Genetics Institute, Cambridge Mass.), among many other suitable adjuvants well known in the art.

Upon immunization with a PIV composition as described herein, via aerosol, droplet, oral, topical or other route, the immune system of the host responds to the vaccine by producing antibodies specific for PIV virus proteins, e.g., F and HN glycoproteins. As a result of the vaccination with an immunogenically effective amount of PIV produced as described herein, the host becomes at least partially or completely immune to PIV infection, or resistant to developing moderate or severe PIV infection, particularly of the lower respiratory tract.

The host to which the vaccines are administered can be any mammal which is susceptible to infection by PIV or a closely related virus and which host is capable of generating a protective immune response to the antigens of the vaccinizing strain. Accordingly, the invention provides methods for creating vaccines for a variety of human and veterinary uses.

The vaccine compositions containing the PIV of the invention are administered to a host susceptible to or otherwise at risk for PIV infection to enhance the host's own immune response capabilities. Such an amount is defined to be a "immunogenically effective dose." In this use, the precise amount of PIV to be administered within an effective dose will depend on the host's state of health and weight, the mode of administration, the nature of the formulation, etc., but will generally range from about $10^3$ to about $10^7$ plaque forming units (PFU) or more of virus per host, more commonly from about $10^4$ to $10^6$ PFU virus per host. In any event, the vaccine formulations should provide a quantity of modified PIV of the invention sufficient to effectively protect the host patient against serious or life-threatening PIV infection.

The PIV produced in accordance with the present invention can be combined with viruses of other PIV serotypes or strains to achieve protection against multiple PIV serotypes or strains. Alternatively, protection against multiple PIV serotypes or strains can be achieved by combining protective epitopes of multiple serotypes or strains engineered into one virus, as described herein. Typically when different viruses are administered they will be in admixture and administered simultaneously, but they may also be administered separately. Immunization with one strain may protect against different strains of the same or different serotype.

In some instances it may be desirable to combine the PIV vaccines of the invention with vaccines which induce protective responses to other agents, particularly other childhood viruses. In another aspect of the invention the PIV can be employed as a vector for protective antigens of other pathogens, such as respiratory syncytial virus (RSV) or measles virus, by incorporating the sequences encoding those protective antigens into the PIV genome or antigenome which is used to produce infectious PIV, as described herein.

In all subjects, the precise amount of recombinant PIV vaccine administered, and the timing and repetition of administration, will be determined based on the patient's state of health and weight, the mode of administration, the nature of the formulation, etc. Dosages will generally range from about $10^3$ to about $10^7$ plaque forming units (PFU) or more of virus per patient, more commonly from about $10^4$ to $10^6$ PFU virus per patient. In any event, the vaccine formulations should provide a quantity of attenuated PIV sufficient to effectively stimulate or induce an anti-PIV immune response, e.g., as can be determined by complement fixation, plaque neutralization, and/or enzyme-linked immunosorbent assay, among other methods. In this regard, individuals are also monitored for signs and symptoms of upper respiratory illness. As with administration to chimpanzees, the attenuated virus of the vaccine grows in the nasopharynx of vaccinees at levels approximately 10-fold or more lower than wild-type virus, or approximately 10-fold or more lower when compared to levels of incompletely attenuated PIV.

In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) PIV infection. Similarly, adults who are particularly susceptible to repeated or serious PIV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered PIV strain expressing a cytokine or an additional protein rich in T cell epitopes may be particularly advantageous for adults rather than for infants.

PIV vaccines produced in accordance with the present invention can be combined with viruses expressing antigens of another subgroup or strain of PIV to achieve protection against multiple PIV subgroups or strains. Alternatively, the vaccine virus may incorporate protective epitopes of multiple PIV strains or subgroups engineered into one PIV clone, as described herein.

The PIV vaccines of the invention elicit production of an immune response that is protective against serious lower respiratory tract disease, such as pneumonia and bronchiolitis when the individual is subsequently infected with wild-type PIV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there are detectable levels of host engendered serum and secretory antibodies which are capable of neutralizing homologous (of the same subgroup)

wild-type virus in vitro and in vivo. In many instances the host antibodies will also neutralize wild-type virus of a different, non-vaccine subgroup.

Preferred PIV vaccine candidates of the invention exhibit a very substantial diminution of virulence when compared to wild-type virus that is circulating naturally in humans. The virus is sufficiently attenuated so that symptoms of infection will not occur in most immunized individuals. In some instances the attenuated virus may still be capable of dissemination to unvaccinated individuals. However, its virulence is sufficiently abrogated such that severe lower respiratory tract infections in the vaccinated or incidental host do not occur.

The level of attenuation of PIV vaccine candidates may be determined by, for example, quantifying the amount of virus present in the respiratory tract of an immunized host and comparing the amount to that produced by wild-type PIV or other attenuated PIV which have been evaluated as candidate vaccine strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold less. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of PIV in the nasopharynx of an infected host are well known in the literature.

Levels of induced immunity provided by the vaccines of the invention can also be monitored by measuring amounts of neutralizing secretory and serum antibodies. Based on these measurements, vaccine dosages can be adjusted or vaccinations repeated as necessary to maintain desired levels of protection. Further, different vaccine viruses may be advantageous for different recipient groups. For example, an engineered PIV strain expressing an additional protein rich in T cell epitopes may be particularly advantageous for adults rather than for infants.

In yet another aspect of the invention the PIV is employed as a vector for transient gene therapy of the respiratory tract. According to this embodiment the recombinant PIV genome or antigenome incorporates a sequence which is capable of encoding a gene product of interest. The gene product of interest is under control of the same or a different promoter from that which controls PIV expression. The infectious PIV produced by coexpressing the recombinant PIV genome or antigenome with the N, P, L and other desired PIV proteins, and containing a sequence encoding the gene product of interest, is administered to a patient. Administration is typically by aerosol, nebulizer, or other topical application to the respiratory tract of the patient being treated. Recombinant PIV is administered in an amount sufficient to result in the expression of therapeutic or prophylactic levels of the desired gene product. Representative gene products which may be administered within this method are preferably suitable for transient expression, including, for example, interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

The following examples are provided by way of illustration, not limitation. These examples document the use of a recombinant cDNA system to introduce an representative mutation into the C ORF which completely silences its expression. Also representative of the invention, mutations involving the introduction of stop codons in the D and V ORFs to silence expression of the corresponding proteins were constructed and evaluated. The effects of these mutations on viral replication and pathogenesis are documented, and the usefulness of these mutations in developing live attenuated vaccine against PIV is thereby established.

In one mutant virus described below, designated rC-KO, expression of the C protein is abrogated by changing the C start codon from methionine to threonine and introducing two stop codons at amino acid positions 7 and 26 of the C ORF. In a second mutant virus. The rC-KO mutant is highly attenuated in vivo and in vivo, as demonstrated using both murine and primate models. rC-KO also conferred substantial protection against challenge with wildtype HPIV3.

Although interruption of the D and V ORFs individually did not significantly affect replication of the virus in vitro or in vivo, interruption of both together attenuated replication in vivo. These results indicate that the C, D and V proteins of HPIV3 each have a role in virus replication, and that the exemplary mutations define powerful tools for developing recombinant PIV vaccine candidates.

EXAMPLE I

Construction of Knock Out Mutations in the HPIV3 C, D, and V ORFs

Cells and Viruses

Human HEp-2 and simian LLC-MK2 monolayer cell cultures were maintained in OptiMEM 1 (Life Technologies, Gaithersburg, Md.) supplemented with 2% fetal bovine serum, gentamicin sulfate (50 ug/mL), and 4 mM glutamine. The modified vaccinia strain Ankara (MVA) recombinant virus that expresses bacteriophage T7 RNA polymerase was generously provided by Drs. L. Wyatt and B. Moss (Wyatt et al., *Virology* 210:202–205, 1995). The JS wildtype (wt) strain of PIV3 and its attenuated ts derivative, JS cp45, were propagated in LLC-MK2 cells as described previously (Hall et al., *Virus Res.* 22:173–184, 1992)).

cDNAs

The full-length cDNA clone encoding the complete 15462 nt antigenome {p3/7(131)2G} of the JS wt virus was described previously (Genebank accession #Z11575) [Durbin et al., *Virology* 235:323–332, 1997; see also, U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059, filed Sep. 19, 1997, each incorporated herein by reference]. This clone was used as the template for the construction of four mutated cDNAs, one in which the expression of the C ORF was completely abrogated, a second and third in which expression of the D and V reading frames was abolished individually, and a fourth in which the D and V reading frame mutations were combined (Table 1, FIG. 1).

The PmlI to BamHI fragment of p3/7(131)2G (nt 1215-3903 of the PIV3 antigenome) was subcloned into the plasmid pUC119 {pUC119(PmlI-BamHI)} which had been modified to include a PmlI site in the multiple cloning region. Site-directed mutagenesis was then performed on pUC119(PmlI-BamHI) using Kunkel's method (Kunkel et al., *Methods Enzymol.* 154:367–382, 1987) to introduce mutations in the C, D and V ORFs which are described below.

Construction of Antigenomic cDNA Encoding the C Knockout Mutant (rC-KO)

Two primers were used to introduce mutations which would silence expression of the C ORF (see Table 1, FIG. 1C). The first mutagenic primer changed the C ORF start codon from ATG to ACG (methionine to threonine) by altering nt position 1795 (T→C) of the full-length antigenome, and changed amino acid position 7 of the C ORF from serine to a stop codon by altering nt position 1813 (C→A). The second mutagenic primer replaced the serine at amino acid position 26 of the C ORF with a stop codon by changing nt position 1869 from C to A. These mutations introduced into the C ORF were silent in the P ORF.

Construction of Antigenomic cDNAs Encoding the D, V, and DV Knockout Mutants (rD-KO, rV-KO, and rDV-KO)

Mutations were introduced which would interrupt expression of both the D and V ORFs individually. The D knockout primer introduced C to A changes at nt positions 2692, 2695, and 2698 of the full length antigenome (Table 1, FIG. 1). These point mutations created three successive stop codons in the putative D ORF which would result in premature termination of the D protein following codon 303 within the 372-amino acid chimeric D protein shown in FIG. 1C. It was not feasible to introduce these stop codons earlier in the D ORF without causing a concomitant coding change in the P ORF. Therefore, expression of the mutated ORF is not completely abrogated but would produce a truncated D protein containing the N-terminal 241 amino acids of P fused to 62, rather than 131, amino acids of the D domain. The V knockout mutagenic primer introduced two point mutations at nt positions 2845 (A to T) and 2854 (C to T) of the full-length antigenome (Table 1). These mutations created stop codons early (aa positions 17 and 20) in the putative V ORF. These mutations were silent in the P ORF, but introduced two amino acid substitutions in the D protein, namely Q354L and A357V. Both primers were used together in a single mutagenesis reaction to create the combined DV knockout mutations.

The Pm1I to BamHI fragment of each full-length clone was sequenced in its entirety to confirm the presence of the introduced mutations and to confirm that other mutations had not been introduced incidentally. These fragments were then separately cloned back into the full-length clone p3/7 (131)2G as previously described (Durbin et al., *Virology* 235:323–332, 1997) to create the four different antigenomic cDNA clones.

EXAMPLE II

Recovery and Characterization of Recombinant C Knockout (rC-KO), D Knockout (rD-KO), V Knockout (rV-KO), and DV Knockout (rDV-KO) Mutants The full-length antigenomic cDNAs bearing either the C, D, V, or DV knockout mutations were transfected into HEp-2 cells on six-well plates (Costar, Cambridge, Mass.) together with the support plasmids {pTM(N), pTM (P no C), and pTM (L)} using LipofectACE (Life Technologies) and the cells were simultaneously infected with MVA-T7 as previously described Durbin et al., *Virology* 235:323–332, 1997; see also, U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference). pTM(P no C) is identical to the pTM(P) plasmid described previously (Id.) with the exception that the C translational start site had been mutated from ATG to ACG, changing the first amino acid in the C ORF from methionine to threonine. After incubation at 32° C. for three days, the transfection harvest was passaged onto a fresh LLC-MK2 cell monolayer in a T25 flask and incubated for 5 days at 32° C. (referred to as passage 1). The amount of virus present in the D, V, and the DV knockout passage 1 harvests was determined by plaque titration on LLC-MK2 monolayer cultures with plaques visualized by immunoperoxidase staining with PIV3 HN-specific monoclonal antibodies as described previously (Id.). The C knockout virus appeared to grow poorly and so its passage 1 harvest was further amplified by a second passage in a monolayer of LLC-MK2 cells in a T75 flask. The amount of virus present in the passage 2 harvest was determined as described above.

The D, V, and DV knockout viruses present in the supernatants of passage 1 harvest were then plaque purified three times on LLC-MK2 cells as previously described (Hall et al., *Virus Res.* 22:173–184, 1992, incorporated herein by reference). The C knockout virus could not be biologically cloned by plaque purification because it was unable to form readily identifiable plaques. Therefore, it was terminally diluted using two-fold dilutions on 96-well plates (12 wells per dilution) of LLC-MK2 cells. The biologically cloned recombinant viruses from the third round of plaque purification or terminal dilution were then amplified twice in LLC-MK2 cells at 32° C. to produce virus for further characterization.

Sequence Analysis of Recovered Recombinant Viruses

Virus was concentrated from clarified medium from infected cell monolayers by polyethylene glycol precipitation as described previously (Durbin et al., *Virology* 235:323–332, 1997). The RNA was purified with TRIzol reagent (Life Technologies) following the manufacturer's recommended procedure. RT-PCR was performed with the Advantage RT-for-PCR kit (Clontech, Palo Alto, Calif.) following the recommended protocol. Control reactions were identical except that reverse transcriptase was omitted from the reaction to confirm that the PCR products were derived solely from viral RNA and not from possible contaminating cDNA. Primers were used to generate the PCR fragment spanning nucleotides 1595–3104 of the full-length antigenome. This fragment includes the entire C, D and V ORFs of the recombinant viruses. The resultant PCR products were then sequenced using cycle dideoxynucleotide sequence analysis (New England Biolabs, Beverly, Mass.).

Protein Analysis by Immunoprecipitation

Two PIV3 C-specific antisera were raised in rabbits by the multiple antigen peptide (MAP) technique against two different C peptides (Research Genetics, Huntsville, Ala.). The two peptides spanned amino acid regions 30–44 and 60–74 of the C protein. Eight copies of each C peptide were placed on a branched carrier core and injected separately into rabbits (two rabbits per peptide) with Freund's adjuvant. The rabbits were boosted with the designated MAP at 2 and 4 weeks and bled at 4, 8, and 10 weeks. Each antiserum recognized the C peptide used as an immunogen in high titer and precipitated C protein from HPIV3 infected cells in a radioimmunoprecipitation assay (RIPA). Similarly, we attempted to produce antisera against the D and V proteins, but were unseccessful; the antisera raised was of low titer against the peptide itself, and we were unable to detect the D or V proteins putatively produced by cells infected with wild type virus.

T25 cell monolayers of LLC-MK2 cells were infected at a multiplicity of infection (MOI) of 5 with either rC-KO, recombinant JS wt virus (rJS) or were mock infected and incubated at 32° C. At 24 hours post-infection, the monolayer was washed with methionine-minus DMEM (Life Technologies) and incubated in the presence of 10 uCi/u of $^{35}S$ methionine in methionine-minus DMEM for an additional 6 hours. The cells were then harvested, washed 3 times, and resuspended in 1 ml RIPA buffer {1% (w/v) sodium deoxycholate, 1% (v/v) Triton X-100, 0.2% (w/v) SDS, 150 mM NaCl, 50 mM Tris-HCl, pH 7.4}, freeze-thawed and pelleted at 6500×g. The cell extract was transferred to a fresh eppendorf tube and a mixture of both C antisera (5 ul each) was added to each sample and incubated with constant mixing for 2 hours at 4° C. 10 ul of a mixture of mAb 454/11 and 101/1, which recognize the HN glycoprotein of HPIV3 (van Wyke Coelingh et al., *J Virol.* 61:1473–1477, 1987), were added to each sample to confrm that recovered virus was indeed HPIV3. Immune complexes were precipitated by adding 200 ul of a 10% suspension of protein A Sepharose beads (Sigma, St. Louis, Mo.) to each sample follow ed by constant mixing at 4° C. overnight. Each sample was denatured, reduced, and analyzed on a 4–12% polyacrylamide gel (NuPAGE, Novex, San Diego, Calif.) per the manufacturer's recommendations. The gel was dried and analyzed by autoradiography.

Multicycle Replication of rPIV3s

Monolayers of LLC-MK2 cells in T25 flasks were infected in duplicate with rCKO, rDV-KO, or rJS at an MOI of 0.01 and incubated at 32° C. in 5% $CO_2$. 250 ul samples were removed from each flask at 24 hour intervals for 7 consecutive days and was flash frozen. An equivalent volume of fresh media was replaced at each time point. Each sample was titered on LLC-MK2 cell monolayers in 96-well plates incubated for 7 days at 32° C. Virus was detected by hemadsorption and reported as $log_{10}TCID_{50}$/ml.

Animal Studies

4–6 week-old golden Syrian hamsters in groups of 21 were inoculated intranasally with 0.1 ml per animal of EMEM (Life Technologies) containing $10^5$ PFU of either rC-KO, rDV-KO, rJS, cp45 (the biologically-derived live attenuated derivative of JS wt virus), or respiratory syncytial virus (RSV). On days 3, 4, and 5 post-inoculation, 5 hamsters from each group, except those which received RSV, were sacrificed and the lungs and nasal turbinates harvested. The nasal turbinates and lungs were homogenized to prepare a 10% or 20% w/v suspension in L-15 (Quality Biologicals, Gaithersburg, Md.) respectively, and the samples were rapidly frozen. Virus present in the samples was titered on 96 well plates of LLC-MK2 cell monolayers incubated at 32° C. for 7 days. Virus was detected by hemadsorption and the mean $log_{10}TCID_{50}$/g was calculated for each day for each group of five hamsters. Sera were collected from the remaining 6 hamsters in each group on days 0 and 28 post-inoculation. Serum antibody responses to each virus was evaluated by hemagglutination-inhibition (HAI) assay as previously described (van Wyke Coelingh et al., *Virology* 143:569–582, 1985). On day 28 the remaining hamsters in each group, including those immunized with RSV, were challenged intranasally with $10^6$ PFU of biologically-derived PIV3 JS wt virus. The animals were sacrificed on day 4 post-challenge and the lungs and nasal turbinates were harvested and processed as described above. The quantity of virus present in the challenge samples was determined as described above. A separate study was performed in which rD-KO and rV-KO were administered to hamsters as described above except that the animals were not challenged.

African Green monkeys (AGMs) in groups of 4 animals each were inoculated intranasally and intratracheally with $10^6$ PFU of either rC-KO, rDV-KO, JSwt, or cp45 as previously described for earlier studies in rhesus monkeys (Durbin et al., *Vaccine* 16:1324–30, 1998). Nasopharyngeal swab samples were collected daily for 12 consecutive days post-inoculation and tracheal lavage samples were collected on days 2, 4, 6, 8, and 10 post-inoculation. The specimens were flash frozen and stored at −70° C. until all specimens had been collected. Virus present in the samples was titered on LLC-MK2 cell monolayers in 96 well plates that were incubated at 32° C. for 7 days. Virus was detected by hemadsorption and the mean $log_{10}TCID_{50}$/ml was calculated for each day. Serum was collected from each monkey on days 0 and 28, and the PIV3 HAI antibody response to experimental infection with the various mutants and the PIV3 wild type (JS) was determined. On day 28 post-inoculation, the AGMs were challenged with $10^6$ PFU of the biologically-derived PIV3 wild type virus administered in a 1 ml inoculum intranasally and intratracheally. Nasopharyngeal swab samples were collected on days 0, 1, 2, 4, 6, 8, 10, and 12 post-challenge and tracheal lavage samples were collected on days 2, 4, 6, 8, and 10 post-challenge. Specimens were flash frozen, stored, and virus present was titered as described above.

Recovery of Recombinant Mutants rC-KO, rD-KO, rV-KO, and rDV-KO

HPIV3 antigenomic cDNAs were prepared to encode the following four mutant viruses (see Table 1, FIG. 1): (i) rC-KO, in which the C ORF was modified to change the initiating codon from M to T and introduce translational stops at codons 7 and 26; (ii) rD-KO, in which translational stops were introduced at codons 304, 305 and 306 in the 372-amino acid chimeric D protein; (iii) rV-KO, in which stop codons were introduced at positions 17 and 20 in the V ORF; and (iv) rDV-KO, in which the mutations in ii and iii were combined. Each mutation was translationally silent in the overlapping ORFs except in the case of the two stop codons introduced into the V ORF (iii) which resulted in two amino acid substitutions in D, namely Q354L and A357V which could not be avoided. Furthermore, the stop codons in D were not introduced earlier in the ORF because they would have altered P. Each mutation was introduced together with a translationally silent restriction site marker (Table 1).

TABLE 1

Nucleotide changes introduced into rPIV3 to yield rC-KO, rD-KO, rV-KO, and rDV-KO[3] viruses.

| rPIV3 designation | Amino acid substitution | Nucleotide sequence of wt/mutated sequence[1] | Restriction enzyme site introduced |
|---|---|---|---|
| rC-KO, mutation #1 | Met-1 to Thr<br>Ser-7 to Stop | 1794-ATG CTA AAA ACT ATC AAA TCA TGG (SEQ ID NO. 1)<br>ACG CTA AAA ACT ACC AAA <u>TAA</u> TGG (SEQ ID NO. 2) | PIIM I |
| rC-KO, mutation #2 | Ser-26 to Stop | 1859-CCT CGG CCC TCA ACA TCA TTG (SEQ ID NO. 3)<br>CCA GCG GCG <u>TAA</u> ACA TCA TTG (SEQ ID NO. 4) | BssH II |
| rD-KO | Ser-304 to Stop[2]<br>Ser-305 to Stop<br>Ser-306 to Stop | 2676-CCT CAT CAT GGA ATC TCA TCA TCG ACA AC (SEQ ID NO. 5)<br>CGA GCT CAT GGA ATC <u>TAA</u> <u>TAA</u> <u>TAG</u> ACA AC (SEQ ID NO 6) | Sac I |

TABLE 1-continued

Nucleotide changes introduced into rPIV3 to yield rC-KO, rD-KO, rV-KO, and rDV-KO[3] viruses.

| rPIV3 designation | Amino acid substitution | Nucleotide sequence of wt/mutated sequence[1] | Restriction enzyme site introduced |
|---|---|---|---|
| rV-KO | Arg-355 to Stop<br>Gln-358 to Stop | 2830-GGA AAG GAA GGA TAC AGA AGA GAG CAA TCG SEQ ID NO. 7<br>GGA GCG GAA GGA TAC TGA AGA GAG TAA TCG (SEQ ID NO. 8) | BsrB I |

The nucleotide sequence of each mutated region is shown and compared with wildtype (wt) sequence. The first nucleotide in each sequence is numbered according to its position in the complete antigenone RNA. Bolded sequence indicates introduced mutations, italicized sequence indicates the introduced restriction enzyme site, and underlined sequence indicates an introduced stop codon.

[2]Numbered according to the sequence of the D fusion of protein combinging the N-terminal 241 aa of P fused to the C-terminal 131 aa of D (FIG. 1B).

[3]The mutations described for rD-KO and rV-KO wre combined to create the rDV-KO virus.

The antigenomic cDNAs were transfected into HEp-2 cells along with the three PIV3 support plasmids {pTM(P no C), pTM(N), pTM(L)} and the cells were simultaneously infected with MVA expressing the T7 RNA polymerase. The efficiency of recovery of rPIV3 containing the mutations in the C, D, or V ORFs was compared with that of a similarly transfected-infected HEp-2 cell culture using the p3/7(131) 2G, the plasmid expressing full-length PIV3 antigenome from which recombinant JSwt PIV3 (rJS) was previously recovered (Durbin et al., *Virology* 235:323–332, 1997). After incubation for 3 days at 32° C. the transfected cells were harvested, and each supernatant was passaged onto a fresh monolayer of LLC-MK2 cells in a T25 flask and incubated for 5 days at 32° C. (passage 1). After 5 days at 32° C., the LLC-MK2 cell monolayer of rJS, rD-KO, rV-KO, and rDV-KO exhibited 3–4+ cytopathic effect (CPE). The corresponding passage 1 of rC-KO exhibited minimal, if any, CPE. Because it was unclear if the lack of CPE in the rC-KO sample was due to a high level of growth restriction of the mutant virus or simply due to very low initial recovery of virus, passage 1 was harvested and the supernatant was passaged onto a fresh monolayer of LLC-MK2 cells in a T75 flask and incubated for 7 days at 32° C. (passage 2). The T75 monolayer of LLC-MK2 cells exhibited only 1–2+ CPE after 7 days of incubation, but the presence of HPIV3 was confirmed by hemadsorption. After three rounds of biological cloning by plaque isolation or terminal dilution, each recombinant mutant was amplified twice in LLC-MK2 cells to produce a suspension of virus for further characterization.

To confirm that the recovered viruses indeed were the expected rC-KO, rD-KO, rV-KO, and rDV-KO mutants, each cloned virus was analyzed by RT-PCR using a primer pair which amplified a fragment of DNA spanning nt 1595–3104 of the HPIV3 antigenome, which includes the portion of the P gene containing the C, D, and V ORFs. The generation of each PCR product was dependent upon the inclusion of RT, indicating that each was derived from RNA and not from contaminating cDNA. The PCR product of rC-KO, rD-KO, rV-KO, and rDV-KO were then digested with restriction enzymes introduced as markers (Table 1), and the presence of the restriction enzyme sites was confirmed. Nucleotide sequencing was also done on the RT-PCR products to confirm the presence of the introduced mutations. All of the introduced mutations were confirmed to be present in the RT-PCR fragment spanning nt 1595–3104 amplified from each cloned recombinant, and other incidental mutations were not found in this fragment.

Figure 3:
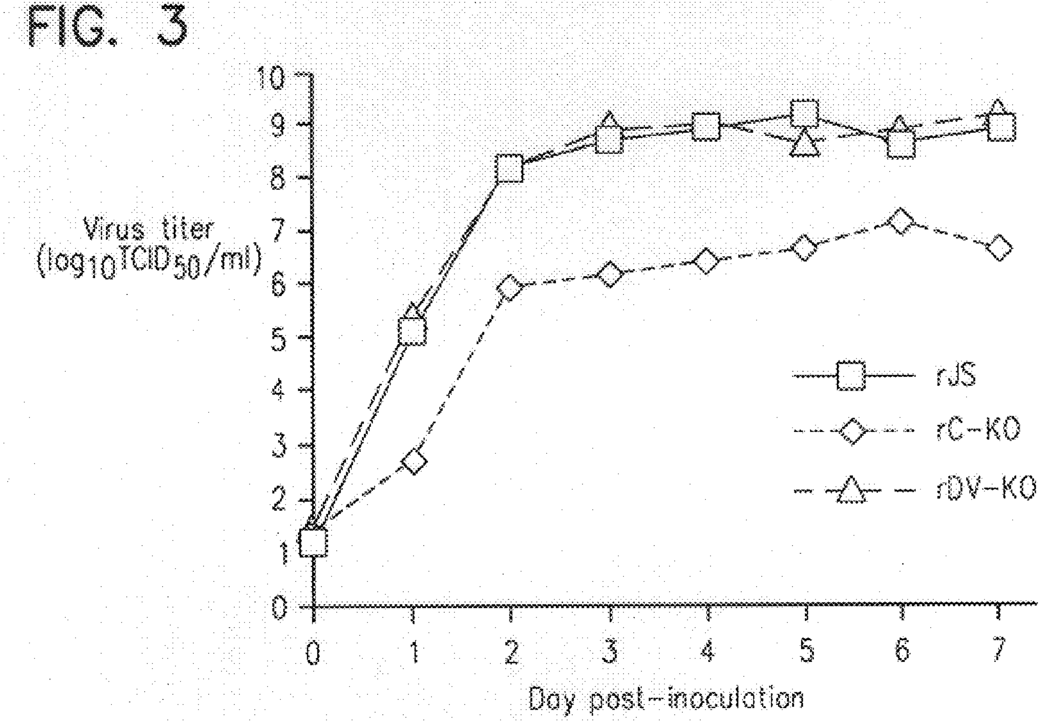
FIG. 3 shows the results of multicycle replication of the exemplary knock out mutants rC-KO, and rDV-KO compared with the parent virus rJS. The virus titers are shown as $TCID_{50}$/ml and are the average of duplicate samples.

To confirm that the C ORF had indeed been silenced, radioimmunoprecipitation assays (RIPA) were performed to compare the rC-KO mutant virus with the rJS wt virus. Cells were infected, incubated in the presence of $^{35}$S methionine from 24 to 30 h post-infection, and cell lysates were prepared. Equivalent amounts of the total protein were incubated with anti-C and anti-HN antibodies and the antibody was then bound to protein A sepharose beads. rJS wt encoded both the HN and C proteins whereas rC-KO failed to express the C protein (FIG. 3).

Replication of rC-KO and rDV-KO in Cell Culture

Duplicate cultures of LLC-MK2 cell monolayers were infected with rC-KO, rDV-KO or rJS at an MOI of 0.01 and incubated for 7 days at 32° C. Medium from each culture was sampled at 24 hour intervals and this material was subsequently titered to evaluate the replication of each virus in cell culture. Replication of rDV-KO was essentially indistinguishable from that of the parent rJS wt with regard to both the rate of virus production and the peak titer (FIG. 3) as well as the ability to replicate at elevated temperature (data not shown). In contrast, the rC-KO virus replicated more slowly and reached a peak titer on day 6 which was 100 to 1,000-fold lower than that of rJS. Thus, the lack of expression of the C protein had a significant effect on virus replication in cell culture.

Replication of rC-KO, rD-KO, rV-KO, and rDV-KO in Hamsters

We then compared the mutant viruses and the rJS wt parent for the ability to replicate in the upper and lower respiratory tract of hamsters. A preliminary study showed that the rD-KO and rV-KO viruses were indistinguishable from the rJS virus in this assay (data not shown) and they were excluded from further evaluation. In a second study, groups of hamsters were inoculated intranasally with $10^5$ pfu per animal of rC-KO, rDV-KO, rJS, or cp45, the biologically-derived vaccine candidate. Compared to rJS, replication of rC-KO was reduced one thousand-fold or greater in both the upper and lower respiratory tracts of the hamsters on each day tested (Table 2) and was as attenuated as the cp45 vaccine candidate virus. Although the replication of rDV-KO was not reduced in the upper respiratory tract of the hamsters, it was reduced at least 20-fold in the lower respiratory tract (Table 2) on each of the three days tested. The hamsters which were infected with rC-KO, rDV-KO, cp45, or rJS had a significant antibody response to HPIV3 and exhibited a high level of restriction of replication of PIV3 challenge virus (Table 3). The protection afforded by rC-KO in the upper respiratory tract was incomplete, but still substantial.

TABLE 2

The rC-KO is attenuated in the upper and lower respiratory tracts of hamsters, and the rDV-kO virus is attenuated in the lower respiratory tract of hamsters.

| | Mean virus titer ($log_{10}TCID_{50}/g$) ± S.E.[2] on indicated day post-infection | | | | | | Peak virus titer ($log_{10}$ $TCID_{50}/g$) ± S.E. | |
|---|---|---|---|---|---|---|---|---|
| | Day 3 | | Day 4 | | Day 5 | | | |
| Virus[1] | Nasal turb. | Lungs | Nasal turb. | Lungs | Nasal turb. | Lungs | Nasal turb. | Lungs |
| cp45 | 4.7 ± 0.2 | 2.7 ± 0.2 | 5.0 ± 0.5 | 2.8 ± 0.5 | 5.4 ± 0.3 | 1.6 ± 0.2 | 5.4 ± 0.3 (D)[3] | 2.8 ± 0.5 (C)[3] |
| rC-KO | 3.4 ± 0.2 | 2.9 ± 0.1 | 3.6 ± 0.1 | 2.1 ± 0.3 | 2.9 ± 0.4 | 1.6 ± 0.2 | 3.6 ± 0.1 (C) | 2.9 ± 0.1 (C) |
| rDV-KO | 7.2 ± 0.2 | 5.5 ± 0.3 | 6.9 ± 0.2 | 4.6 ± 0.1 | 5.4 ± 0.1 | 5.9 ± 0.2 | 7.2 ± 0.2 (A) | 5.9 ± 0.2 (B) |
| rJS | 6.7 ± 0.3 | 6.8 ± 0.5 | 7.4 ± 0.2 | 6.6 ± 0.4 | 6.6 ± 0.2 | 7.2 ± 0.2 | 7.4 ± 0.2 (A) | 7.2 ± 0.2 (A) |

[1]. Groups of 5 hamsters were inoculated intranasally with $10^5$ pfu of indicated virus. cp45 is a biologically-derived virus, and the others are recombinant viruses.
[2]. Standard error
[3]. Means in each column with a different letter are significantly different (a = 0.05) by Duncan's Multiple Range test whereas those with the same letter are not significantly different.

TABLE 3

The rC-KO and rDV-KO viruses are immunogenic and protective against challenge with PIV3 wt virus in hamsters.

| Immunizing virus[1] | Serum HAI antibody titer (reciprocal mean $log_2$ ± S.E.) | Response to Challenge Mean PIV3 titer2 ($log_{10}TCID_{50}/g$) Nasal Turb. | Lungs |
|---|---|---|---|
| rC-KO | 7.3 ± 0.4 | 3.3 ± 0.5 | <1.2 ± 0.0 |
| rDV-KO | 11.3 ± 0.2 | <1.5 ± 0.0 | <1.2 ± 0.0 |
| cp45 | 11.8 ± 0.3 | <1.5 ± 0.0 | <1.2 ± 0.0 |
| rJS | 12.1 ± 0.2 | <1.5 ± 0.0 | <1.2 ± 0.0 |
| RSV | <2.0 ± 0.0 | 7.0 ± 0.2 | 4.7 ± 0.3 |

[1]. Indicates virus used to immunize groups of six hamsters on Day 0.
[2]. On day 28, all hamsters were bled to determine the serum HAI antibody titer and were challenged with $10^6$ PFU biologically-derived JS wt HPIV3. Lungs and nasal turbinates were harvested on day 4 post-challenge.

Replication of rC-KO and rDV-KO in Primates

To further evaluate the attenuation phenotype and protective efficacy of rC-KO and rDV-KO, these mutants were each administered to a group of four AGMs, and their replication in the upper and lower respiratory tracts was compared with that of cp45 and JSwt. Replication of rC-KO was 100-fold or more reduced in the upper respiratory tract of the AGMs, whereas rDV-KO was 10-fold reduced at this site. The attenuation observed for these two viruses in the upper respiratory tract was comparable to that of cp45 (Table 4). Although rC-KO was highly attenuated (more than $10^5$-fold) in the lower respiratory tract of the AGMs, rDV-KO was only modestly (<10-fold) restricted at this site. Both viruses induced an HAI antibody response to HPIV3 although the HAI response of AGMs to rC-KO, like that of hamsters, was significantly less than that of the other viruses (Table 4). The immunized AGMs were challenged on day 28 with $10^6$ PFU biologically-derived JS wt virus given IN and IT. The animals which had received rJS, rDV-KO or the cp45 vaccine candidate virus were completely protected against replication of challenge virus in both the upper and lower respiratory tracts of the AGMs. The protection conferred by rC-KO against replication of challenge virus was substantial although not complete. Peak titers of challenge virus were significantly reduced in both the upper and lower respiratory tracts of animals in this group and the duration of shedding of virus from the upper and lower respiratory tracts was reduced from 10 days to 4 days and from 8 days to 6 days respectively.

Summarizing the above disclosure, the results herein demonstrate successful recovery of infectious HPIV3 from cDNA to construct novel recombinant viruses in which expression of the C, D, or V ORFs were individually interrupted by an exemplary ablation technique involving mutations that alter an amino acid specifying an initiation codon and/or the introduction of translational stop codons. In another exemplary viral clone, the D and V ORFs were interrupted together. These examples reveal the importance of the accessory C, D, and V ORFs of HPIV3 to virus replication in vitro and in vivo, and provide useful vaccine candidates for prevention and treatment of PIV. In particular, the level of replication of rC-KO in the upper and lower respiratory tract of AGMs was slightly below that of cp45, the most promising PIV3 vaccine candidate strain. Despite its reduced replication in vivo, rC-KO was able to induce a sufficient immune response to restrict replication of HPIV3 challenge virus, qualifying this recombinant as a useful vaccine candidate, although it may need to be given at a higher dose such as $10^{7.0}$TCID or in multiple doses to humans to achieve a higher level of restriction of replication of wt virus.

Using recombinant DNA technology, mutations identified in the HPIV3 mutant cp45 have been introduced singly and in combination into the JS wt sequence (Skiadopoulos et al., *J Virol.* 73:1374–1381, 1999; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference). This has allowed identification of the mutations that contribute to the attenuation, temperature-sensitive (ts), and/or cold-adapted phenotypes of this vaccine candidate. These mutations, and other modifications of recombinant PIV disclosed herein, are useful adjunctive mutations to adjust the level of attenuation, as well as immunogenicity and other desired phenotypic characteristics, of recombinant PIV of the invention having C, D, and or V ORF knock out mutations.

The two other proteins which potentially are encoded within the P locus are the V and D proteins. With the exception of HPIV-1, all Respiroviruses, Morbilliviruses, and Rubulaviruses contain an intact V ORF. The cysteine-rich C-terminal portion of the V ORF is the most conserved ORF of the P gene in Paramyxovirinae and appears to be expressed by all these viruses except HPIV1 and HPIV3. Although HPIV3 contains the V ORF, it is unclear how it is accessed, but the fact that it has remained intact suggests that it is utilized. Unlike the V cistron of the Paramyxoviridae, the D protein is unique to human and bovine PIV3. The D protein is accessed by insertion of two non-templated G residues at the editing site of the P mRNA resulting in a fusion protein in which the N-terminal 241 amino acids of P are fused with the C-terminal 131 amino acids of the D ORF. Nothing is known about the function of the D protein, and it has not yet been identified in HPIV3 infected cells or virions, although an edited mRNA capable of encoding D has been detected. (Galinski et al., *Virology* 186:543–550, 1992.) In an attempt to address this issue we recovered a recombinant HPIV3 mutant which contained three successive stop codons in the D ORF which would express a truncated fusion protein containing 61 amino acids encoded by the D ORF. Neither of the recombinants having a single D or V ORF knock out mutation were significantly restricted in replication in vivo or in vivo. However, these mutations are nonetheless highly useful for development of PIV vaccine candidates. This is illustrated by the successful recovery of a combinatorial V and D knock out mutant, which was made by combining the two sets of mutations to create multiple stop codons in both the V and D ORFs. This mutant, designated rDV-KO, was restricted in its replication in the lower respiratory tract of hamsters as well as in both the upper and lower respiratory tract of AGMs. Because the P ORF was unaffected by the introduced mutations, it is reasonable to assume that the phenotypes we observed reflect the loss of V and D activity. Although replication of rDV-KO was attenuated in vivo, replication in cell culture was essentially unchanged. These results provides compelling evidence that the D and V proteins of wildtype HPIV3 are expressed and that functional abrogation of both together is responsible for the in vivo attenuation phenotype demonstrated by rDV-KO. It is possible that these proteins are interacting with one another on a molecular level to affect in vivo replication.

Although the foregoing invention has been described in detail by way of example for purposes of clarity of understanding, it will be apparent to the artisan that certain changes and modifications may be practice within the scope of the appended claims which are presented by way of illustration not limitation.

What is claimed is:

1. An isolated infectious recombinant parainfluenza virus (PIV) comprising a PIV genome or antigenome, a nucleocapsid protein (N), a phosphoprotein (P), and a large polymerase protein (L), wherein a modification is introduced in the genome or antigenome comprising a partial or complete deletion of one or more C, D or V ORF(s) or one or more nucleotide change(s) that reduces or ablates expression of said one or more C, D or V ORF(s).

2. The recombinant PIV of claim 1, wherein expression of said one or more C, D or V ORF(s) is reduced or ablated by introduction of one or more stop codons.

3. The recombinant PIV of claim 1, wherein expression of said one or more C, D or V ORF(s) is reduced or ablated by a mutation in an RNA editing site or by a mutation that alters the amino acid specified by an initiation codon.

4. The recombinant PIV of claim 1, wherein expression of said one or more C, D or V ORF(s) is reduced or ablated by introduction of a frame shift mutation.

5. The recombinant PIV of claim 1, wherein said one or more C, D or V ORF(s) is deleted in whole or in part.

6. The recombinant PIV of claim 1, wherein the modification introduced in the genome or antigenome comprises a partial or complete deletion of the C ORF or one or more nucleotide change(s) that reduces or ablates expression of the C ORF.

7. The recombinant PIV of claim 6, wherein expression of the C ORF is reduced or ablated by introduction of one or more stop codons.

8. The recombinant PIV of claim 7, wherein the C ORF start codon is changed to a threonine codon by a nucleotide change at position 1795 of said genome or antigenome and two stop codons are introduced by altering nucleotides 1813 and 1869.

9. The recombinant PIV of claim 6 which is rC-KO.

10. The recombinant PIV of claim 1, wherein the modification introduced in the genome or antigenome comprises a partial or complete deletion of the D ORF or one or more nucleotide change(s) that reduces or ablates expression of the D ORF.

11. The recombinant PIV of claim 9, wherein expression of the D ORE is reduced or ablated by introduction of one or more stop codons.

12. The recombinant PIV of claim 10, wherein three stop codons are introduced by nucleotide change at positions 2692, 2695, and 2698 of said antigenome.

13. The recombinant PIV of claim 9 which is rD-KO.

14. The recombinant PIV of claim 1, wherein the modification introduced in the genome or antigenome comprises a partial or complete deletion of the V ORF or one or more nucleotide change(s) that reduces or ablates expression of said V ORF.

15. The recombinant PIV of claim 12, wherein expression of the V ORF is reduced or ablated by introduction of one or more stop codons.

16. The recombinant PIV of claim 13, wherein two stop codons are introduced by nucleotide change at positions 2845 and 2854 of said antigenome.

17. The recombinant PIV of claim 13 which is rV-KO.

18. The recombinant PIV of claim 1, wherein the modification introduced in the genome or antigenome comprises a partial or complete deletion at least two of said C, D or V ORF(s) or one or more nucleotide change(s) that reduces or ablates expression of at least two of said C, D or V ORF(s).

19. The recombinant PIV of claim 18, wherein the D and V ORFs are both modified by a partial or complete deletion or one or more nucleotide change(s) that reduces or ablates their expression.

20. The recombinant PIV of claim 18 which is rDV-KO.

21. The recombinant PIV of claim 1, wherein the modification in the genome or antigenome specifies one or more desired phenotypic changes in the recombinant PIV selected from (i) attenuation in cell culture, (ii) attenuation in the upper and/or lower respiratory tract of a mammalian host, (iii) a change in viral plaque size, (iv) a change in cytopathic effect, and (v) a change in immunogenicity.

22. The recombinant PIV of claim 21, wherein viral growth in cell culture is attenuated by approximately 5–10-fold or greater compared to growth of the corresponding wild-type or mutant parental PIV strain.

23. The recombinant PIV of claim 21, wherein viral growth in the upper and lower respiratory tract is attenuated by approximately 10–100 fold or greater compared to growth of the corresponding wild-type or mutant parental PIV strain.

24. The recombinant PIV of claim 23, wherein viral growth in the upper and lower respiratory tract is attenuated by approximately 100–1,000 fold or greater compared to growth of the corresponding wild-type or mutant parental PIV strain.

25. The recombinant PIV of claim 1, wherein the genome or antigenome is further modified by introduction of one or more attenuating mutations identified in a biologically derived mutant human PIV.

26. The recombinant PIV of claim 25, wherein the genome or antigenome incorporates at least one and up to a full complement of attenuating mutations present within PIV3 JS cp45.

27. The recombinant PIV of claim 25, wherein the genome or antigenome incorporates at least one and up to a full complement of attenuating mutations specifying an amino acid substitution at Tyr 942, Leu 992, and/or Thr 1558 in the PIV3 L gene; Val 96 and Ser 389 in N; Ile96 in C; Ile420 and/or Ala 550 in F; Val 384 in HN, and/or nucleotide substitution in the 3' leader at position 23, 24, 28, and/or 45 and/or at position 62 in the gene start sequence of N.

28. The recombinant PIV of claim 25, wherein the genome or antigenome incorporates at least two attenuating mutations.

29. The recombinant PIV of claim 25, wherein the genome or antigenome includes at least one attenuating mutation stabilized by multiple nucleotide changes in a codon specifying the mutation.

30. The recombinant PIV of claim 1, wherein the genome or antigenome comprises an additional nucleotide modification specifying a phenotypic change selected from a change in growth characteristics, attenuation, temperature-sensitivity, cold-adaptation, plaque size, host-range restriction, or a change in immunogenicity.

31. A method for stimulating the immune system of an individual against PIV which comprises administering to the individual an immunologically sufficient amount of the recombinant PIV of claim 1 combined with a physiologically acceptable carrier.

32. The method of claim 31, wherein the recombinant PIV is administered in a dose of $10^3$ to $10^7$ PFU.

33. The method of claim 31, wherein the recombinant PIV is administered to the upper respiratory tract.

34. The method of claim 31, wherein the recombinant PIV is administered by spray, droplet or aerosol.

35. The method of claim 31, wherein the recombinant PIV and a second attenuated PIV are administered simultaneously as a mixture.

36. An immunogenic composition to elicit an immune response against PIV comprising an immunogenically sufficient amount of the recombinant PIV of claim 1 in a physiologically acceptable carrier.

37. The immunogenic composition of claim 36, formulated in a dose of $10^3$ to $10^7$ PFU.

38. The immunogenic composition of claim 36, formulated for administration to the upper respiratory tract by spray, droplet or aerosol.

39. The immunogenic composition of claim 36, wherein the recombinant PIV elicits an immune response against one or more viruse(s) selected from HPIV1, HPIV2 and HPIV3.

40. The immunogenic composition of claim 39, wherein the recombinant PIV elicits an immune response against HPIV3 and another virus selected from HPIV1, HPIV2 and HPIV3.

41. An isolated polynucleotide molecule comprising a recombinant PIV genome or antigenome which incorporates a nucleotide modification comprising a partial or complete deletion of one or more C, D or V ORF(s) or one or more nucleotide change(s) that reduces or ablates expression of said one or more C, D or V ORF(s).

42. The isolated polynucleotide molecule of claim 41, wherein expression of said one or more C, D or V ORF(s) is reduced or ablated by introduction of one or more stop codons, by a mutation in an RNA editing site, or by a mutation that alters the amino acid specified by an initiation codon.

43. The isolated polynucleotide molecule of claim 41, wherein said one or more C, D or V ORF(s) is deleted in whole or in part.

44. The isolated polynucleotide molecule of claim 41, wherein the modification introduced in the genome or antigenome comprises a partial or complete deletion of the C ORF or one or more nucleotide change(s) that reduces or ablates expression of the C ORF.

45. The isolated polynucleotide molecule of claim 41, wherein the modification introduced in the genome or antigenome comprises a partial or complete deletion of the D ORF or one or more nucleotide change(s) that reduces or ablates expression of the D ORF.

46. The isolated polynucleotide molecule of claim 41, wherein the modification introduced in the genome or antigenome comprises a partial or complete deletion of the V ORF or one or more nucleotide change(s) that reduces or ablates expression of the V ORF.

47. The isolated polynucleotide molecule of claim 41, wherein the modification introduced in the genome or antigenome comprises a partial or complete deletion of at least two of said C, D or V ORF(s) or one or more nucleotide change(s) that reduces or ablates expression of at least two of said C, D or V ORF(s).

48. The isolated polynucleotide molecule of claim 41, wherein the D and V ORFs are both modified by a partial or complete deletion or one or more nucleotide change(s) that reduces or ablates their expression.

49. The isolated polynucleotide molecule of claim 41, wherein the recombinant genome or antigenome is further modified by one or more attenuating mutations.

50. The isolated polynucleotide molecule of claim 41, further comprising a nucleotide modification specifying a phenotypic change selected from a change in growth characteristics, attenuation, temperature-sensitivity, cold-adaptation, plaque size, host-range restriction, or a change in immunogenicity.

51. A method for producing an infectious attenuated recombinant PIV particle from one or more isolated polynucleotide molecules encoding said PIV, comprising:

expressing in a cell or cell-free lysate an expression vector comprising an isolated polynucleotide comprising a recombinant PIV genome or antigenome which incorporates a nucleotide modification comprising a partial or complete deletion of one or more C, D or V ORF(s) or one or more nucleotide change(s) that reduces or ablates expression of said one or more C, D or V ORF(s), and PIV N, P, and L proteins.

52. The method of claim 51, wherein the chimeric PIV genome or antigenome and the N, P, and L proteins are expressed by two or more different expression vectors.

53. An expression vector comprising an operably linked transcriptional promoter, a polynucleotide sequence encoding a PIV genome or antigenome which incorporates a nucleotide modification comprising a partial or complete deletion of one or more C, D or V ORF(s) or one or more nucleotide change(s) that reduces or ablates expression of said one or more C, D or V ORF(s), and a transcriptional terminator.

* * * * *

SEQUENCE LISTING

```
<160> NUMBER OF SEQ ID NOS: 11

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Recombinant
      sequence incorporating rD-KO mutation

<400> SEQUENCE: 1

atgctaaaaa ctatcaaatc atgg                                              24


<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Recombinant
      sequence incorporating rD-KO mutation

<400> SEQUENCE: 2

acgctaaaaa ctaccaaata atgg                                              24


<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Recombinant
      sequence incorporating rD-KO mutation

<400> SEQUENCE: 3

cctcggccct caacatcatt g                                                 21


<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Recombinant
      sequence incorporating rD-KO mutation

<400> SEQUENCE: 4

ccagcgcgct aaacatcatt g                                                 21
```

-continued

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Recombinant sequence incorporating rD-KO mutation

<400> SEQUENCE: 5
cctcatcatg gaatctcatc atcgacaac 29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Recombinant sequence incorporating rD-KO mutation

<400> SEQUENCE: 6
cgagctcatg gaatctaata atagacaac 29

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Wild type sequence adjacent site rV-KO mutation

<400> SEQUENCE: 7
ggaaaggaag gatacagaag agagcaatcg 30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Recombinant sequence incorporating rV-KO mutation

<400> SEQUENCE: 8
ggagcggaag gatactgaag agagtaatcg 30

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Sequence incorporating RNA editing site motif

<400> SEQUENCE: 9
aaaaaagggg g 11

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Sequence incorporating translational start sites of P and C open reading frames

<400> SEQUENCE: 10
gttgatggaa agcgatgcta 20

-continued

```
<210> SEQ ID NO 11
<211> LENGTH: 13
<212> TYPE: DNA
<213> ORGANISM: Artificial Sequence
<220> FEATURE:
<223> OTHER INFORMATION: Description of Artificial Sequence: Partial
      sequence of P mRNA having insertion of two G
      residues in editing site

<400> SEQUENCE: 11

aaaaaagggg ggg                                                      13
```